(12) United States Patent
Bitto et al.

(10) Patent No.: US 8,333,121 B2
(45) Date of Patent: *Dec. 18, 2012

(54) MEASURING SYSTEM FOR MEDIA FLOWING IN A PIPELINE

(75) Inventors: Ennio Bitto, Aesch (CH); Alfred Rieder, Landshut (DE); Martin Anklin, Dornach (CH); Christof Huber, Bern (CH); Michael Kirst, Lörrach (DE)

(73) Assignee: Endress + Hauser Flowtec AG, Reinach (CH)

( * ) Notice: Subject to any disclaimer, the term of this patent is extended or adjusted under 35 U.S.C. 154(b) by 320 days.

This patent is subject to a terminal disclaimer.

(21) Appl. No.: 12/659,534

(22) Filed: Mar. 11, 2010

(65) Prior Publication Data

US 2010/0242623 A1   Sep. 30, 2010

Related U.S. Application Data

(66) Substitute for application No. 61/213,742, filed on Jul. 9, 2009.
(60) Provisional application No. 61/202,543, filed on Mar. 11, 2009.

(30) Foreign Application Priority Data

Mar. 11, 2009  (DE) .......................... 10 2009 001 472
Jul. 9, 2009   (DE) .......................... 10 2009 027 580

(51) Int. Cl.
 *G01F 1/84*   (2006.01)
(52) U.S. Cl. ................................................. 73/861.357
(58) Field of Classification Search .................. None
See application file for complete search history.

(56) References Cited

U.S. PATENT DOCUMENTS

| | | | |
|---|---|---|---|
| 5,661,232 A | 8/1997 | Van Cleve et al. | |
| 2002/0174730 A1 | 11/2002 | Drahm et al. | |
| 2006/0000293 A1* | 1/2006 | Rieder et al. | 73/861.357 |
| 2010/0236338 A1* | 9/2010 | Bitto et al. | 73/861.357 |
| 2010/0242624 A1* | 9/2010 | Bitto et al. | 73/861.357 |

(Continued)

FOREIGN PATENT DOCUMENTS

| | | |
|---|---|---|
| DE | 10 2004 030 392 | 1/2006 |
| EP | 0 119 638 | 9/1984 |
| EP | 2 159 552 | 3/2010 |

OTHER PUBLICATIONS

International Preliminary Examination Report in corresponding International Application No. PCT/EP2010/053127.
International Search Report in corresponding International Application No. PCT/EP2010/053127.

*Primary Examiner* — Harshad R Patel
(74) *Attorney, Agent, or Firm* — Bacon & Thomas, PLLC

(57) ABSTRACT

A measuring system comprises: a measuring transducer, through which medium flows and which produces oscillatory signals dependent on medium viscosity and/or a Reynolds number of the flowing medium; and transmitter electronics for driving the measuring transducer and for evaluating oscillatory signals. The measuring transducer includes: four, mutually spaced, flow openings; an outlet-side flow divider with four, mutually spaced, flow openings; four, mutually parallel, straight, measuring tubes for conveying flowing medium, connected to the flow dividers electromechanical exciter mechanism. The transmitter electronics feeds, by means of an electrical driver signal supplied to the exciter mechanism, electrical excitation power into the exciter mechanism, while the exciter mechanism converts electrical excitation power at least partially into torsional oscillations of the first measuring tube, opposite-equal torsional oscillations of the second measuring tube, as well as into torsional oscillations of the third measuring tube, opposite-equal torsional oscillations of the fourth measuring tube.

48 Claims, 8 Drawing Sheets

U.S. PATENT DOCUMENTS

| | | | |
|---|---|---|---|
| 2011/0146383 A1* | 6/2011 | Bitto et al. | 73/30.03 |
| 2011/0146416 A1* | 6/2011 | Bitto et al. | 73/861.357 |
| 2011/0167907 A1* | 7/2011 | Bitto et al. | 73/32 A |
| 2011/0259123 A1* | 10/2011 | Bitto et al. | 73/861.357 |
| 2011/0265580 A1* | 11/2011 | Huber et al. | 73/861.357 |
| 2012/0048034 A1* | 3/2012 | Hussain et al. | 73/861.357 |

* cited by examiner

MEASURING SYSTEM FOR MEDIA FLOWING IN A PIPELINE

CROSS-REFERENCE TO RELATED APPLICATION

This is a Nonprovisional Application which claims the benefit of U.S. Provisional Application Ser. No. 61/202,543, filed on Mar. 11, 2009 and U.S. Provisional Application Ser. No. 61/213,742, filed on Jul. 9, 2009.

TECHNICAL FIELD

The invention relates to a measuring system for measuring a viscosity and/or a Reynolds number of a medium flowing in a pipeline, especially an aqueous liquid, a slurry, a paste, or other flowing material. The measuring system includes a measuring transducer of vibration-type, as well as a transmitter electronics connected thereto.

BACKGROUND DISCUSSION

In the field of process measurements and automation technology, for measuring physical parameters, such as e.g. the mass flow, density and/or viscosity of media flowing in pipelines, often such measuring systems formed as inline measuring devices of compact construction are used, which, by means of a measuring transducer of vibration-type through which the medium flows, and a transmitter electronics connected thereto, effect reaction forces in the medium, such as e.g. Coriolis forces corresponding with the mass flow, inertial forces corresponding with the density of the medium, and/or frictional forces corresponding with the viscosity of the medium, and, derived from these, produce a measurement signal representing the respective mass flow, density and/or viscosity of the medium. Such measuring transducers, in part embodied also as multivariable Coriolis mass flow/viscosity meters or Coriolis mass flow/density/viscometer, are described in detail in e.g. EP-A 1 001 254, EP-A 553 939, U.S. Pat. No. 4,793,191, US-A 2002/0157479, US-A 2006/0150750, US-A 2007/0151368, US-A 2010/0050783, U.S. Pat. Nos. 5,370,002, 5,602,345, 5,796,011, 6,308,580, 6,415,668, 6,711,958, 6,920,798, 7,134,347, 7,392,709, WO-A 96/08697, WO-A 03/027616, WO-A 2008/059262, WO-A 2009/120222 or WO-A 2009/120223.

Each of the measuring transducers includes a transducer housing, which is formed from an inlet-side, first housing end, at least partially by means of two or four, first flow divider, having in each case circularly cylindrical or conical flow openings spaced apart from one another, and from an outlet-side, second housing end formed at least partially by means of two or four, second flow divider, having in each case flow openings spaced apart from one another. In the case of at least some of the measuring transducers illustrated in U.S. Pat. Nos. 5,602,345, 5,796,011, 7,350,421, or US-A 2007/0151368, the transducer housing comprises a rather thick walled, circularly cylindrical tube segment, which forms at least a middle segment of the transducer housing.

For conveying the at least sometimes flowing medium, the measuring transducers comprise furthermore, in each case, at least two measuring tubes connected for parallel flow—in each case straight, or in each case equally curved—made of metal, especially steel or titanium, which tubes are placed within the transducer housing, and are oscillatably held therein by means of the aforementioned flow dividers. A first of the equally constructed measuring tubes, extending parallel to the other, opens into a first flow opening of the inlet-side, first flow divider with an inlet-side, first measuring tube end, and into a first flow opening of the outlet-side, second flow divider with an outlet-side, second measuring tube end. A second of the measuring tubes opens into in a second flow opening of the first flow divider with an inlet-side, first measuring tube end, and into a second flow opening of the second flow divider with an outlet-side, second measuring tube end. Each of the flow dividers includes additionally, in each case, a flange with a sealing surface for the fluid-tight connecting of the measuring transducer to pipe segments of the pipeline serving to supply the medium to, or to carry the medium away from, the measuring transducer.

The measuring tubes of known measuring systems of the aforementioned type are caused to vibrate during operation for the purpose of producing the aforementioned reaction forces, driven in the so-called driven, or wanted, mode by an exciter mechanism serving to produce or maintain mechanical oscillations of the measuring tubes—in this case, bending oscillations about an imaginary oscillation axis, which imaginarily connects the respective first and second measuring tube ends. The oscillations in the wanted mode are, particularly also in applications of the measuring transducer in measuring systems formed as Coriolis mass flow- and/or density measuring devices, developed as lateral bending oscillations, and bear superimposed thereon, in the case of medium flowing through the measuring tubes, as a result of Coriolis forces induced therein, additional, equal frequency oscillations in the so-called Coriolis mode. Accordingly, the exciter mechanism—here most often electrodynamic—in the case of straight measuring tubes, is embodied in such a manner that the two measuring tubes in the wanted mode at least partially—most often, however, predominantly—can be excited differentially to opposite phase bending oscillations in a shared plane of oscillation; that is, by entry of exciter forces simultaneously along a shared line of action, however, acting in opposite directions by means of at least one oscillation exciter linked just to the two measuring tubes. As, among other things, evident from the mentioned US-A 2006/0150750, based on opposite phase bending oscillations of two measuring tubes, besides mass flow and density, the viscosity of the medium conveyed in the measuring transducer can also be ascertained, for instance, based on an electrical excitation power, fed from the transmitter electronics to the exciter mechanism, serving to overcome the damping of the measuring tube oscillations caused also particularly by the medium located in the measuring tubes.

For registering of vibrations, especially of oscillations of the measuring tubes excited by the exciter mechanism, and for producing oscillation measurement signals serving as vibration representing, primary signals of the measuring transducer, the measuring transducers have additionally, in each case, a sensor arrangement, most often likewise electrodynamic, which reacts to relative movements of the measuring tubes. Typically, the sensor arrangement is formed by means of an inlet-side oscillation sensor, registering oscillations of the measuring tubes differentially—thus only relative movements of the measuring tubes—as well as of an outlet-side oscillation sensor, also registering oscillations of the measuring tubes differentially. Each of the normally equally constructed oscillation sensors is formed by means of a permanent magnet held on the first measuring tube, and a cylindrical coil, permeated by the magnetic field of the permanent magnet, held on the second measuring tube.

In operation, the above described tube arrangement, formed by means of the at least two measuring tubes, with the, in each case shared holding of the exciter mechanism and the sensor arrangement of the measuring transducer, is excited by means of the electromechanical exciter mechanism, at least at times, in the wanted mode, to execute mechanical oscillations at at least one, dominating, wanted oscillation frequency. As oscillation frequency for the oscillations in the wanted mode, in such case, usually an instantaneous natural eigen, or resonance, frequency of the tube arrangement is selected, which frequency, in turn, is essentially dependent on the size, shape and material of the measuring tubes as well as on an instantaneous density of the medium. As a result of the fluctuating density of the medium to be measured, and/or as a result of performing a change of media during operation, the wanted oscillation frequency is variable during operation of the measuring transducer naturally at least within a calibrated and, insofar, predetermined, wanted frequency band, which correspondingly has a predetermined lower and a predetermined upper limit frequency.

For defining a free oscillatory length of the measuring tubes, and associated therewith, for adjusting the wanted frequency band, measuring transducers of the above described type comprise additionally most often at least one inlet-side coupling element for forming inlet-side oscillation nodes for opposite phase vibrations, especially bending oscillations, of both measuring tubes, which element is affixed to both measuring tubes spaced apart from both flow dividers, as well as at least one outlet-side coupling element for the forming of outlet-side oscillation nodes for opposite phase vibrations, especially bending oscillations of the measuring tubes, which element is affixed to both measuring tubes, spaced apart from both flow dividers as well as from the inlet-side coupling element. In the case of straight measuring tubes, a minimum distance between inlet side and outlet side coupling elements—insofar as they belong to the tube arrangement—corresponds to, in such case, the free oscillatory length of the measuring tubes. By means of the coupling elements, additionally an oscillation quality factor of the tube arrangement, such as the sensitivity of the measuring transducer, can also be, on the whole, influenced in such a manner that, for a minimum required sensitivity of the measuring transducer, at least one minimum free oscillatory length is to be provided.

Development in the field of measuring transducers of vibration-type in the meantime has reached a state such that modern measuring transducers of the described type can, for practical purposes, satisfy highest requirements with respect to precision and reproducibility of the measurement results for a broad application spectrum in the field of flow measurement technology. As a result, such measuring transducers are used in practice for applications with mass flow rates from only a few g/h (grams per hour) up to some t/min (tons per minute), at pressures of up to 100 bar for liquids or even over 300 bar for gases. Due to the high bandwidth of their opportunities for use, industrial grade measuring transducers of vibration-type are available with nominal diameters (corresponding to the caliber of the pipeline to be connected to the measuring transducer, or to the caliber of the measuring transducer measured at the connecting flange), which lie in a nominal diameter range between 1 mm and 250 mm, and are specified for maximum nominal mass flow rate 2200 t/h, respectively, for pressure losses of less than 1 bar. A caliber of the measuring tubes lies, in such case, for instance, in a region between 80 mm and 100 mm.

As already mentioned, with measuring systems having measuring tubes executing bending oscillations, the viscosity, or also measured variables dependent upon it, such as, for instance, the Reynolds number, can also be ascertained, measurable based on the viscosity, and, indeed, also with bending oscillations (see also US-A 2006/0150750) However, in the case of this method, particularly also as a result of the often very small amplitude of the wanted oscillations, the sensitivity of the measuring transducer can have a certain dependency on the nominal diameter, and, indeed, in such a manner that the sensitivity decreases with the increasing nominal diameter. As a result, also the accuracy of measurement can become less with the increasing nominal diameter, or the respective transmitter electronics is presented with increased requirements with regard to signal processing technology and computing power. In spite of this, in the meantime, measuring transducers are also available for the purposes of measuring viscosity for use in pipelines with very high mass flow rates, and associated therewith, very large calibers of over 50 mm; there is quite a significant interest in measuring transducers of high precision and low pressure loss also for viscosity measurements in the case of still greater pipeline calibers, for instance, 100 mm or more, or mass flow rates of 1200 t/h or more, to be used, for instance, for applications in the petrochemical industry, or in the area of transporting and handling petroleum, natural gas, fuels, etc. This leads, in the case of a correspondingly scaled enlargement of already established measuring transducer concepts known from the state of the art, especially as set forth in EP-A 1 001 254, EP-A 553 939, U.S. Pat. No. 4,793,191, US-A 2002/0157479, US-B 2007/0151368, U.S. Pat. Nos. 5,370,002, 5,796,011, 6,308,580, 6,711,958, 7,134,347, 7,350,421, or WO-A 03/027616, to the fact that the geometric dimensions—especially the installed length corresponding to a distance between the sealing surfaces of both flanges, and in the case of curved measuring tubes, to a maximum lateral expansion of the measuring transducer—especially as resulting from the desired oscillation characteristics, the required loading capacity, as well as the maximum allowed pressure loss, would become very large. Associated therewith, also the empty mass of the measuring transducer unavoidably increases, with conventional measuring transducers of large nominal diameters already implemented having an empty mass of, for instance, 400 kg. For measuring transducers with two bent measuring tubes, for instance, according to U.S. Pat. Nos. 7,350,421 or 5,796,011, investigations have been performed concerning their scaling to still greater nominal diameters. These investigations have shown, for example, that for nominal diameters of more than 300 mm, the empty mass of a conventional measuring transducer enlarged to scale would lie well over 500 kg, along with an installed length of more than 3000 mm and a maximum lateral expansion of more than 1000 mm. As a result, it can be understood that industrial grade, even series-manufacturable, measuring transducers of conventional design and materials with nominal diameters of well over 300 mm will, both for reasons of technical feasibility and due to economic considerations, not be available in the foreseeable future.

SUMMARY OF THE INVENTION

Based on the above recited state of the art, consequently, an object of the invention is to provide a measuring transducer suited for precisely measuring a viscosity or Reynolds number, also having a high accuracy of measurement in the case of large mass flow rates of more than 1200 t/h and, associated therewith, large nominal diameters of over 100 mm, while exhibiting a construction, which is as compact as possible.

For achieving the object, the invention resides in a measuring system for a medium flowing in a pipeline, for example, an aqueous liquid, a slurry, a paste or other flowing material. The measuring system, for instance embodied as a compact measuring device and/or as a Coriolis mass flow/viscosity measuring device, comprises a measuring transducer of vibration-type, through which the medium flows during operation, for producing oscillation signals dependent on a viscosity and/or a Reynolds number of the flowing medium, as well as a transmitter electronics electrically coupled with the measuring transducer for driven the measuring transducer and for evaluating the oscillation signals delivered by the measuring transducer. The measuring transducer comprises a, for example, essentially tubular and/or externally circularly cylindrical, transducer housing, of which an inlet-side, first housing end is formed by means of an inlet-side, first flow divider having exactly four, for example, circularly cylindrical, tapered or conical, flow openings spaced, in each case, from one another, and an outlet-side, second housing end is formed by means of an outlet-side, second flow divider having exactly four, for example, circularly cylindrical, tapered or conical, flow openings spaced, in each case, from one another, exactly four, straight measuring tubes forming flow paths arranged for parallel flow and connected to the, for example, equally constructed, flow dividers for guiding flowing medium, especially, measuring tubes held oscillatably in the transducer housing only by means of said flow dividers and/or equally constructed and/or at least pairwise parallel relative to one another, as well as an electromechanical exciter mechanism for exciting and maintaining mechanical oscillations of the at least two measuring tubes, for example, torsional oscillations or torsional/bending oscillations. Of the four measuring tubes, especially measuring tubes equally constructed as regards shape, variable and material, a first measuring tube, for example, a circularly cylindrical, first measuring tube, opens with an inlet-side, first measuring tube end into a first flow opening of the first flow divider, and with an outlet-side, second measuring tube end into a first flow opening of the second flow divider, a second measuring tube, for example, a circularly cylindrical, first measuring tube, opens with an inlet-side, first measuring tube end into a second flow opening of the first flow divider, and with an outlet-side, second measuring tube end into a second flow opening of the second flow divider, a third measuring tube, for example, a circularly cylindrical, third measuring tube, opens with an inlet-side, first measuring tube end into a third flow opening of the first flow divider, and with an outlet-side, second measuring tube end into a third flow opening of the second flow divider, and a fourth measuring tube, for example, a circularly cylindrical, fourth measuring tube, opens with an inlet-side, first measuring tube end into a fourth flow opening of the first flow divider, and with an outlet-side, second measuring tube end into a fourth flow opening of the second flow divider. Moreover, the transmitter electronics feeds electrical excitation power, particularly electrical excitation power with a variable maximum voltage level and/or a variable maximum electrical current level, into the exciter mechanism by means of a variable and/or, at least at times, periodic, first electrical driver signal supplied to the exciter mechanism, for example, with at least one signal frequency corresponding to an eigenfrequency of a natural mode of oscillation of the tube arrangement, while the exciter mechanism converts the electrical excitation power, particularly dependent also on a voltage level and electrical current level of the first driver signal, at least at times, at least partially, into torsional oscillations of the first measuring tube and into torsional oscillations of the second measuring tube, which are opposite and equal (hereinafter opposite-equal) to the torsional oscillations of the first measuring tube, as well as into torsional oscillations of the third measuring tube and into torsional oscillations of the fourth measuring tube, which are opposite-equal to the torsional oscillations of the third measuring tube.

According to a first embodiment of the invention, it is additionally provided that the exciter mechanism converts electrical excitation power into torsional oscillations of the first measuring tube, and into torsional oscillations of the second measuring tube opposite-equal to the torsional oscillations of the first measuring tube, as well as into torsional oscillations of the third measuring tube, and into torsional oscillations of the fourth measuring tube opposite-equal to the torsional oscillations of the third measuring tube in such a manner that simultaneously both a middle segment of the first measuring tube executes rotary oscillations about an imaginary torsional oscillation axis perpendicular to a cross section of said tube segment, a middle segment of the second measuring tube executes rotary oscillations about an imaginary torsional oscillation axis perpendicular to a cross section of said tube segment, a middle segment of the third measuring tube executes rotary oscillations about an imaginary torsional oscillation axis perpendicular to a cross section of said tube segment, and a middle segment of the fourth measuring tube executes rotary oscillations about an imaginary torsional oscillation axis perpendicular to a cross section of said tube segment and/or that simultaneously each of the measuring tubes executes torsional oscillations in a torsional oscillation fundamental mode having a single oscillatory antinode.

According to a second embodiment of the invention, it is additionally provided that the tube arrangement is embodied such that it has an first imaginary longitudinal section plane, in which extends a longitudinal axis of the first measuring tube, which axis imaginarily connects the first and second ends of said first measuring tube, as well as a longitudinal axis of the second measuring tube, which axis imaginarily connects the first and second ends of said second measuring tube, and extends parallel to the longitudinal axis of the first measuring tube, and a second imaginary longitudinal section plane, which is spaced from, and parallel to the first imaginary longitudinal section plane and in which both extends a longitudinal axis of the third measuring tube, which axis imaginarily connects the first and second ends of said third measuring tube, as well as also a longitudinal axis of the fourth measuring tube, which axis imaginarily connects the first and second ends of said fourth measuring tube, and extends parallel to the longitudinal axis of the first measuring tube.

According to a third embodiment of the invention, it is additionally provided that the first measuring tube has a caliber which is equal to a caliber of the second measuring tube, for example, also equal to a caliber of the third measuring tube as well as equal to a caliber of the fourth measuring tube.

According to a fourth embodiment of the invention, it is additionally provided that the first oscillation exciter is so embodied and arranged in the measuring transducer such that the line of action, with which the exciter forces produced by the first oscillation exciter are introduced into the tube arrangement, has a perpendicular distance to the first imaginary longitudinal section plane of the tube arrangement, which is greater than a fourth of a caliber of the first measuring tube, especially greater than 35% of the caliber of the first measuring tube, and/or smaller than 200% of the caliber of the first measuring tube, especially smaller than 100% of the caliber of the first measuring tube.

According to a fifth embodiment of the invention, it is additionally provided that the exciter mechanism effects oscillations of the measuring tubes, for example, opposite-equal torsional oscillations of the first and second measuring tubes, or opposite-equal bending/torsional oscillations of the first and second measuring tubes, by the feature that an exciter force acting on the first measuring tube, generated by means of the first oscillation exciter, acts opposite, for example, opposite-equal, to an exciter force acting on the second measuring tube, generated simultaneously by means of the first oscillation exciter.

According to a sixth embodiment of the invention, it is additionally provided that the exciter mechanism, for example, simultaneously to the torsional oscillations, effects bending oscillations of the first measuring tube about its longitudinal axis, and bending oscillations of the second measuring tube about its longitudinal axis opposite-equal to the bending oscillations of the first measuring tube, as well as also bending oscillations of the third measuring tube about its longitudinal axis, and bending oscillations of the fourth measuring tube about its longitudinal axis opposite-equal to the bending oscillations of the third measuring tube.

According to a seventh embodiment of the invention, it is additionally provided that the tube arrangement is embodied such that at least one eigenfrequency of natural bending oscillations of the first measuring tube, for example, in such a bending oscillation fundamental mode having a single oscillatory antinode, equals an eigenfrequency of natural torsional oscillations of the first measuring tube, for example, such in a torsional oscillation fundamental mode having a single oscillatory antinode, and such that at least one eigenfrequency of natural bending oscillations of the second measuring tube, for example, such in a bending oscillation fundamental mode having a single oscillatory antinode, equals an eigenfrequency of natural torsional oscillations of the second measuring tube, especially such in a torsional oscillation fundamental mode having a single oscillatory antinode.

According to an eighth embodiment of the invention, it is additionally provided that each of the four measuring tubes, excited by the exciter mechanism, executes bending oscillations, for example, bending oscillations in a bending oscillation fundamental mode having a single oscillatory antinode, coupled with, in each case, torsional oscillations of equal frequency, for example, torsional oscillations in a torsional oscillation fundamental mode having a single oscillatory antinode.

According to a ninth embodiment of the invention, it is additionally provided that the first driver signal has a plurality of signal components with mutually differing signal frequencies, and wherein at least one of the signal components of the first driver signal, for example a dominant signal component with respect to a signal power, has a signal frequency corresponding to an eigenfrequency of a natural mode of oscillation of the tube arrangement, for example a natural torsional oscillation mode of the tube arrangement, in which mode each of the four measuring tubes executes torsional oscillations.

According to an tenth embodiment of the invention, it is additionally provided that, on the basis of an electrical excitation power, especially an electrical excitation power dependent on a voltage level and an electrical current level of the first driver signal, converted in the exciter mechanism, especially at least partially into torsional oscillations of the at least two measuring tubes or at least partially in torsional/bending oscillations of the at least two measuring tubes, the transmitter electronics generates a measured value representing the viscosity of the flowing medium, and/or a measured value representing the Reynolds number of the flowing medium.

According to a eleventh embodiment of the invention, it is additionally provided that, besides the four measuring tubes, the measuring transducer has no additional measuring tube serving to convey flowing medium, and vibrating during operation.

According to a first further development of the invention, it is additionally provided that the exciter mechanism has at least a first oscillation exciter, for example an electrodynamic, first oscillation exciter, which, for example, acts differentially on the at least two measuring tubes, for converting electrical excitation power supplied to the exciter mechanism into changing and/or periodic, mechanical exciter forces, for example forces having at least one signal frequency corresponding to an eigenfrequency of a natural mode of oscillation of the tube arrangement, for effecting the torsional oscillations of the first measuring tube and the torsional oscillations of the second measuring tube opposite-equal to the torsional oscillations of the first measuring tube.

According to a first embodiment of the first further development of the invention, it is additionally provided that the first oscillation exciter has a permanent magnet held at least on the first measuring tube, for example, by means of a coupling element affixed to the first measuring tube and serving as a lever arm for effecting torsional moments that act on the first measuring tube, and a cylindrical coil permeated by magnetic field of the permanent magnet, held on the second measuring tube, for instance, by means of a coupling element affixed at least to the second measuring tube and serving as a lever arm for effecting torsional moments that act on the second measuring tube.

According to a second embodiment of the first further development of the invention, it is additionally provided that the first driver signal is supplied to the first oscillation exciter, especially in such a manner that a first exciter current flows through its cylindrical coil, driven by means of the variable first exciter voltage provided by the first driver signal.

According to a third embodiment of the first further development of the invention, it is additionally provided that the tube arrangement is so embodied, that it has: A first imaginary longitudinal section plane, in which extend both a measuring tube longitudinal axis of the first measuring tube connecting its first and second measuring tube ends imaginarily, as well as also a measuring tube longitudinal axis of the second measuring tube, which imaginarily connects its first and second measuring tube ends and is parallel to the measuring tube longitudinal axis of the first measuring tube; spaced from and parallel to the first imaginary longitudinal section plane, a second imaginary longitudinal section plane, in which extend both a measuring tube longitudinal axis of the third measuring tube imaginarily connecting its first and second measuring tube ends, as well as also a measuring tube longitudinal axis of the fourth measuring tube, which imaginarily connects its first and second measuring tube ends and is parallel to the measuring tube longitudinal axis of the first measuring tube; as well as a third imaginary longitudinal section plane lying between the first longitudinal section plane and second longitudinal section plane, namely a third imaginary longitudinal section plane, in each case, spaced from the first imaginary longitudinal section plane and from the second imaginary longitudinal section plane and parallel, in each case, to the first and second longitudinal section planes; and that the first oscillation exciter converts an electrical excitation power, fed, for instance, by means of the first driver signal, into exciter forces, for example, periodic exciter forces, serving for exciting oscillations of the measuring tubes, for instance, of opposite-equal torsional oscillations of the at least two measuring tubes or of opposite-equal bending/torsional oscillations of the at least two measuring tubes, and introduced into the tube arrangement along a line of action spaced from, and at least approximately parallel to, the third imaginary longitudinal section plane, for instance, also spaced from the first imaginary longitudinal section plane, for example, also extending essentially transversely to the measuring tube longitudinal axis of the first measuring tube and to the measuring tube longitudinal axis of the second measuring tube.

According to a second further development of the invention, it is additionally provided that the transmitter electronics feeds electrical excitation power into the exciter mechanism also by means of a variable and/or, at least at times, periodic, second electrical driver signal supplied to the exciter mechanism, for example, a driver signal having at least one signal frequency corresponding to an eigenfrequency of a natural mode of oscillation of the tube arrangement, and, for example, a second driver signal equal to the first driver signal as regards at least one signal frequency, and/or a second driver signal phase shifted relative to the first driver signal, for example, a second driver signal also having a variable maximum voltage level and/or a variable maximum electrical current level.

According to a first embodiment of the second further development of the invention, it is additionally provided that the exciter mechanism converts electrical excitation power supplied by means of the second driver signal, especially electrical power dependent on a voltage level and an electrical current level also of the second driver signal, at least at times, into torsional oscillations of the third measuring tube for instance equal-opposite to torsional oscillations of the first measuring tube and into torsional oscillations of the fourth measuring tube equal-opposite to the torsional oscillations of the third measuring tube, for instance, also to the torsional oscillations of the second measuring tube, for example, in such a manner that a middle segment of the third measuring tube executes rotary oscillations about an imaginary torsional oscillation axis perpendicular to a cross section of said tube segment, and a middle segment of the fourth measuring tube executes rotary oscillations about an imaginary torsional oscillation axis perpendicular to a cross section of said tube segment, and/or that each of the four measuring tubes executes opposite-equal torsional oscillations in a torsional oscillation fundamental mode having a single oscillatory antinode.

According to a second embodiment of the second further development of the invention, it is additionally provided that the second driver signal has a plurality of signal components with signal frequency varying from one another, and that at least one of the signal components of the second driver signal, for example, a dominant signal component with respect to a signal power, has a signal frequency corresponding to an eigenfrequency of a natural mode of oscillation of the tube arrangement, for example, a natural torsional oscillation mode of the tube arrangement, in which each of the measuring tubes executes opposite-equal torsional oscillations. According to a third embodiment of the second further development of the invention, it is additionally provided that the second driver signal is supplied to an oscillation exciter of the exciter mechanism, for example, in such a manner that a second exciter current passes through a cylindrical coil of said oscillation exciter, driven by means of a variable second exciter voltage provided by the second driver signal.

According to a third further development of the invention, it is additionally provided that the exciter mechanism further has a second oscillation exciter, which is, for example, electrodynamic and/or equally constructed to the first oscillation exciter, and acts differentially on the at least two measuring tubes, for converting electrical excitation power supplied to the exciter mechanism into variable and/or periodic, mechanical exciter forces, for example exciter forces having at least one signal frequency corresponding to an eigenfrequency of a natural mode of oscillation of the tube arrangement, effecting the torsional oscillations of the third measuring tube and the torsional oscillations of the fourth measuring tube opposite-equal to the torsional oscillations of the third measuring tube.

According to a first embodiment of the third further development of the invention, it is additionally provided that the second oscillation exciter is formed from a permanent magnet held at least on the third measuring tube, for example by means of a coupling element affixed to the third measuring tube and serving as a lever arm for effecting torsional moments which act on the third measuring tube, and from a cylindrical coil permeated by the magnetic field of the permanent magnet, held on the fourth measuring tube, for example, by means of a coupling element affixed to the fourth measuring tube, and serving as a lever arm for effecting torsional moments which act on the fourth measuring tube.

According to a second embodiment of the third further development of the invention, it is additionally provided, that the exciter mechanism effects oscillations of the measuring tubes, for example, also opposite-equal torsional oscillations of the third and fourth measuring tube or opposite-equal bending/torsional oscillations of the third and fourth measuring tube, that an exciter force generated by means of the second oscillation exciter and acting on the third measuring tube is opposite to an exciter force generated by means of the second oscillation exciter at the same time and acting, for example, also opposite-equally, on the fourth measuring tube.

According to a third embodiment of the third further development of the invention, it is additionally provided, that the exciter mechanism effects opposite-equal torsional oscillations, for example, also opposite-equal bending/torsional oscillations, of the measuring tubes by the features,
  that the exciter force generated by means of the first oscillation exciter and acting on the first measuring tube is opposite to the force generated by means of the second oscillation exciter at the same time and acting on the third measuring tube exciter force, and
  that the exciter force generated by means of first oscillation exciter and acting on the second measuring tube is opposite to the exciter force generated by means of the second oscillation exciter at the same time and acting on the fourth measuring tube.

According to a fourth further development of the invention, the measuring transducer further includes a sensor arrangement formed, for example, by means of a first oscillation sensor and by means of an equally constructed second oscillation sensor, for, for example, differentially registering mechanical oscillations, for example torsional oscillations or torsion/bending oscillations, of the measuring tubes, and producing at least a first oscillation signal representing mechanical oscillations, for example, torsional oscillations or torsion/bending oscillations, of the measuring tubes.

According to a first embodiment of the fourth further development of the invention, it is provided that the first oscillatory signal delivered by the sensor arrangement represents at least in part torsional oscillations of the first measuring tube, for example, torsional oscillations of the first measuring tube relative to opposite-equal torsional oscillations of the second measuring tube.

According to a second embodiment of the fourth further development of the invention, it is provided that the transmitter electronics, by means of the first oscillation signal, for example on the basis of a signal voltage and/or a signal frequency of the first oscillation signal, generates the measured value representing the viscosity of the flowing medium, and/or a measured value representing the Reynolds number of the flowing medium.

According to a third embodiment of the fourth further development of the invention, the sensor arrangement includes at least a first oscillation sensor, which especially is electrodynamic and/or placed in the measuring transducer on the inlet side, for, for example, differentially registering, for example, inlet-side mechanical oscillations, especially torsional oscillations or torsion/bending oscillations of the measuring tubes, and for producing the first oscillation signal. A further development of this embodiment additionally provides that the first oscillation sensor has a permanent magnet held on the first measuring tube, especially by means of a coupling element, and a cylindrical coil permeated by the magnetic field of the permanent magnet, held on the second measuring tube, for example by means of a coupling element, for producing an electrical voltage serving to form the first oscillation signal of the sensor arrangement.

According to a fourth embodiment of the fourth further development of the invention, the sensor arrangement includes further four oscillation sensors, for example, electrodynamic oscillation sensors and/or equally constructed oscillation sensors and/or, in each case, oscillation sensors equally remote from the first oscillation exciter, for registering, for example, differentially, mechanical oscillations, especially torsional oscillations or torsion/bending oscillations, of the measuring tubes and for producing at least one oscillation signal representing mechanical oscillations, especially torsional oscillations or torsion/bending oscillations, of the measuring tubes. Developing this embodiment further, it is additionally provided, that each of the four oscillation sensors has a permanent magnet held on at least one of the measuring tubes, for example, by means of a coupling element, and a cylindrical coil permeated by the magnetic field of the permanent magnet and held, in each case, on at least one of the other measuring tubes, for example, by means of a coupling element, for producing an electrical voltage serving for forming an oscillation signal of the sensor arrangement.

According to a fifth further development of the invention, the measuring transducer includes further a first, especially plate shaped, coupling element of first type affixed to both the first measuring tube as well as also to the third measuring tube, but, otherwise, to no others of the measuring tubes, for holding components of the first oscillation exciter, especially a cylindrical coil or a permanent magnet, and for introducing an exciter force generated by means of the first oscillation exciter into the first measuring tube, and/or for transforming an exciter force generated by means of the first oscillation exciter into a torsional moment acting on the first measuring tube, as well as a second coupling element of first type, for example a plate shaped, second coupling element of first type and/or a second coupling element of first type equally constructed to the first coupling element of first type, affixed to both the second measuring tube and also to the third measuring tube, but, otherwise, to no others of the measuring tubes, for holding components of the first oscillation exciter, especially a cylindrical coil or a permanent magnet, and for introducing an exciter force generated by means of the first oscillation exciter into the second measuring tube, and/or for converting an exciter force generated by means of the first oscillation exciter into a torsional moment acting on the second measuring tube and into a torsional moment acting on the fourth measuring tube.

According to a fifth embodiment of the fifth further development of the invention, it is provided that the oscillation exciter of the exciter mechanism, in each case, is held on two coupling elements of first type, which lie oppositely to one another, especially in a manner such that a minimum distance between two coupling elements held on the same oscillation exciter is more than twice as large as a tube outer diameter of the first measuring tube.

According to a sixth embodiment of the fifth further development of the invention, it is provided that a permanent magnet of the first oscillation exciter is affixed to the first coupling element of first type, especially on a distal first end of the first coupling element of first type removed from the first measuring tube, and a cylindrical coil of the first oscillation exciter is affixed to the second coupling element of first type, for instance, on a distal first end of the second coupling element of first type removed from the second measuring tube, especially in such a manner that the first coupling element of first type acts as a lever arm, which converts an exciter force generated by the first oscillation exciter at least partially into a torsional moment effecting the torsional oscillations of the first measuring tube, and that the second coupling element of first type acts as a lever arm, which converts an exciter force generated by the first oscillation exciter at least partially into a torsional moment effecting torsional oscillations of the second measuring tube.

According to an seventh embodiment of the fifth further development of the invention, it is provided that the first and second coupling elements of first type are placed oppositely to one another in the measuring transducer.

According to a eighth embodiment of the fifth further development at the invention, it is provided that the first and second coupling elements of first type are placed in the measuring transducer such that both a center of mass of the first coupling element of first type as well as a center of mass of the second coupling element of first type lie within the cross sectional plane, in which extend both the line of action of the exciter forces produced by the first oscillation exciter, as well as the line of action of the exciter forces produced by the second oscillation exciter.

According to a sixth further development of the invention, the measuring transducer further includes a transducer housing, for example, an essentially tubular and/or outwardly circularly cylindrical transducer housing, of which an inlet-side, first housing end is formed by means of the first flow divider, and an outlet-side, second housing end is formed by means of the second flow divider.

A basic idea of the invention is, instead of the conventional measuring systems customarily used to measure viscosity with a single straight measuring tube or two parallel bent measuring tubes through which the medium flows, to use two parallel straight measuring tubes through which the medium flows and which execute during operation at least partially, or at least pairwise, opposite-equal torsional oscillations, and so to enable a high degree of accuracy of measurement for viscosity, with, on the one hand, space saving construction of the measuring system as a whole, and also, on the other hand, acceptable pressure loss over a broad measuring range, especially also in the case of very high mass flow rates of well over 1200 t/h.

An advantage of the measuring transducer of the invention is additionally, among other things, that predominantly established structural designs, as regards, for instance, the materials used, the joining technology, the manufacturing steps, etc, can be applied or must be modified only slightly, whereby also the manufacturing costs, as a whole, are quite comparable to those of conventional measuring transducers. In this respect, a further advantage of the invention can be seen in the fact that thereby not only is an opportunity created to offer comparatively compact measuring systems for viscosity also with large nominal diameters of over 100 mm, especially with a nominal diameter of larger than 120 mm, with manageable geometric dimensions and empty masses, but in addition can be economically sensible to implement. Consequently, the measuring transducer of the invention is especially suitable for measuring flowing media, which are conveyed in a pipeline having a caliber of larger than 100 mm, especially of 150 mm or higher. In addition, the measuring transducer is also suitable for measuring mass flows, which, at least at times, are greater than 1200 t/h, especially at least, at times, more than 1400 t/h, such as can occur e.g. in applications for measuring petroleum, natural gas or other petrochemical substances.

BRIEF DESCRIPTION OF THE DRAWINGS

The invention as well as other advantageous embodiments thereof will now be explained in greater detail on the basis of examples of embodiments presented in the figures of the drawing. Equal parts are provided in all figures with equal reference characters; when required to avoid cluttering the drawing or when it otherwise appears sensible, already mentioned reference characters are omitted in subsequent figures. Other advantageous embodiments or further developments, particularly also combinations of firstly only individually explained aspects of the invention, will become evident additionally from the figures of the drawing, as well as also from the dependent claims themselves.

The figures of the drawing show as follows.

DETAILED DISCUSSION IN CONJUNCTION WITH THE DRAWINGS

FIGS. 1a, 1b, 1c, 2 show, schematically presented, a measuring system 1, especially one embodied as a Coriolis mass flow/viscosity, and/or density/viscosity, measuring device, serving to register a viscosity $\eta$ of a medium flowing in a pipeline (not shown) and to represent in the form of a measured value $X_\eta$, or $X_{RE}$ instantaneously representing said viscosity $\eta$—or also a therefrom derived, measured variable, such as, for instance, a Reynolds number Re of the flow. The medium can be practically any flowable material, for example, an aqueous or oil-like liquid, a slurry, a paste or the like. Alternatively, or in supplementation, the inline measuring device 1 can, in given cases, also be used to measure a density rho and/or a mass flow m of the medium. Especially, the inline measuring device is provided, to measure media, such as e.g. petroleum or other petrochemical substances, which flow in a pipeline having a caliber of greater than 100 mm, especially a caliber of 150 mm or above. Especially, the inline measuring device is additionally provided to measure flowing media of the aforementioned type, which are caused to flow with a mass flow rate of greater than 1200 t/h, especially greater than 1500 t/h. The measuring system, which is here implemented, by way of example, by means of an inline measuring device in compact construction, comprises therefor: A measuring transducer 11 of vibration-type connected via an inlet end as well as an outlet end to the process line, through which measuring transducer flows during operation of the medium to be measured, such as, for instance, a low viscosity liquid and/or a high viscosity paste; as well as a transmitter electronics 12, which is electrically connected with the measuring transducer 11, for instance, by means of a multi-veined connecting cable or corresponding single lines, and which, during operation, is supplied for example, from the exterior via connecting cable and/or by means of internal energy storer, with electrical energy, for driven the measuring transducer and for evaluating oscillatory signals delivered by the measuring transducer.

Figure 1A:
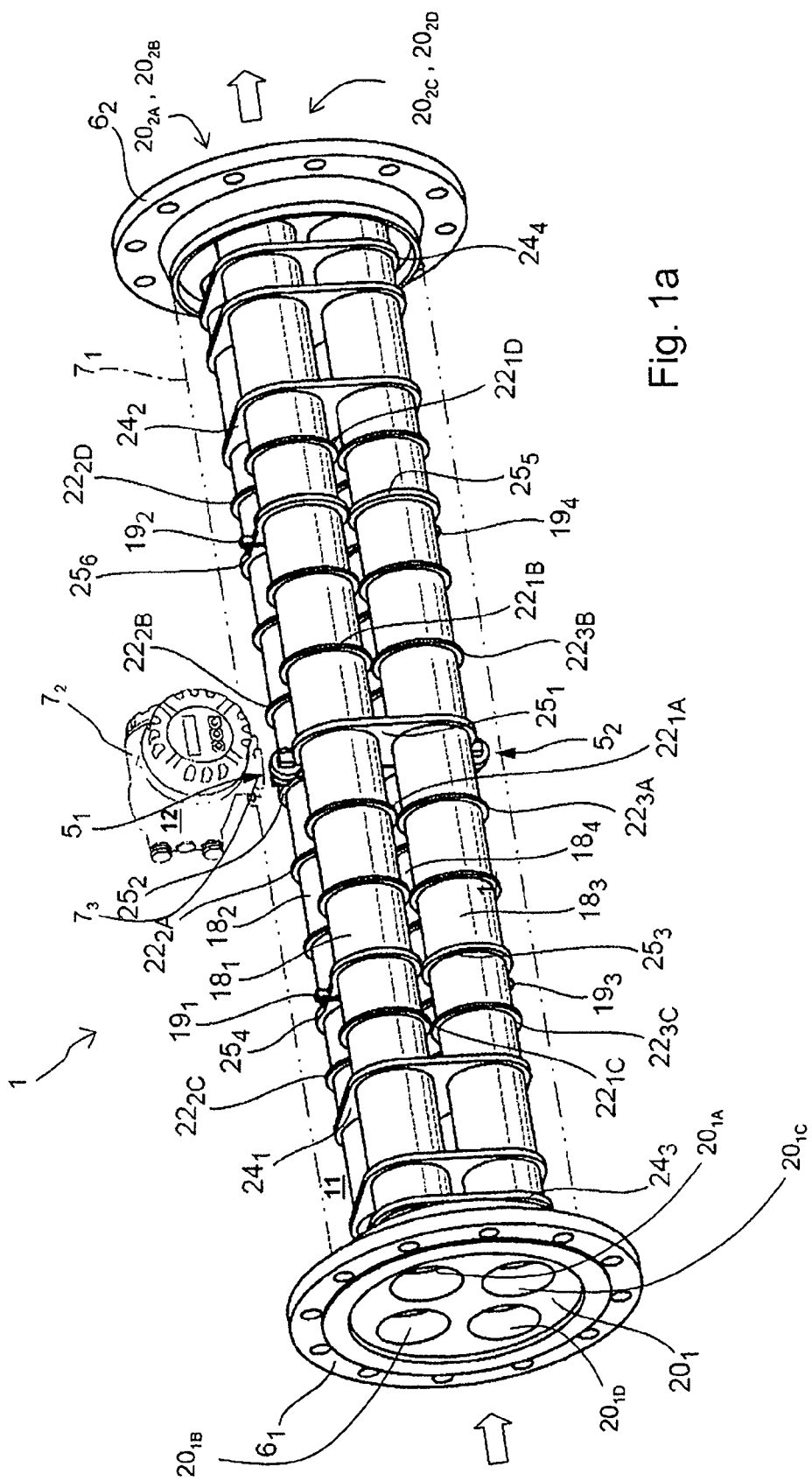
FIGS. 1a, 1b, and 1c a measuring system, for example, embodied as a Coriolis mass flow/density/viscosity, measuring device in compact construction, in partially transparent, side view with a measuring transducer of vibration-type and thereto connected transmitter electronics.
Figure 1B:
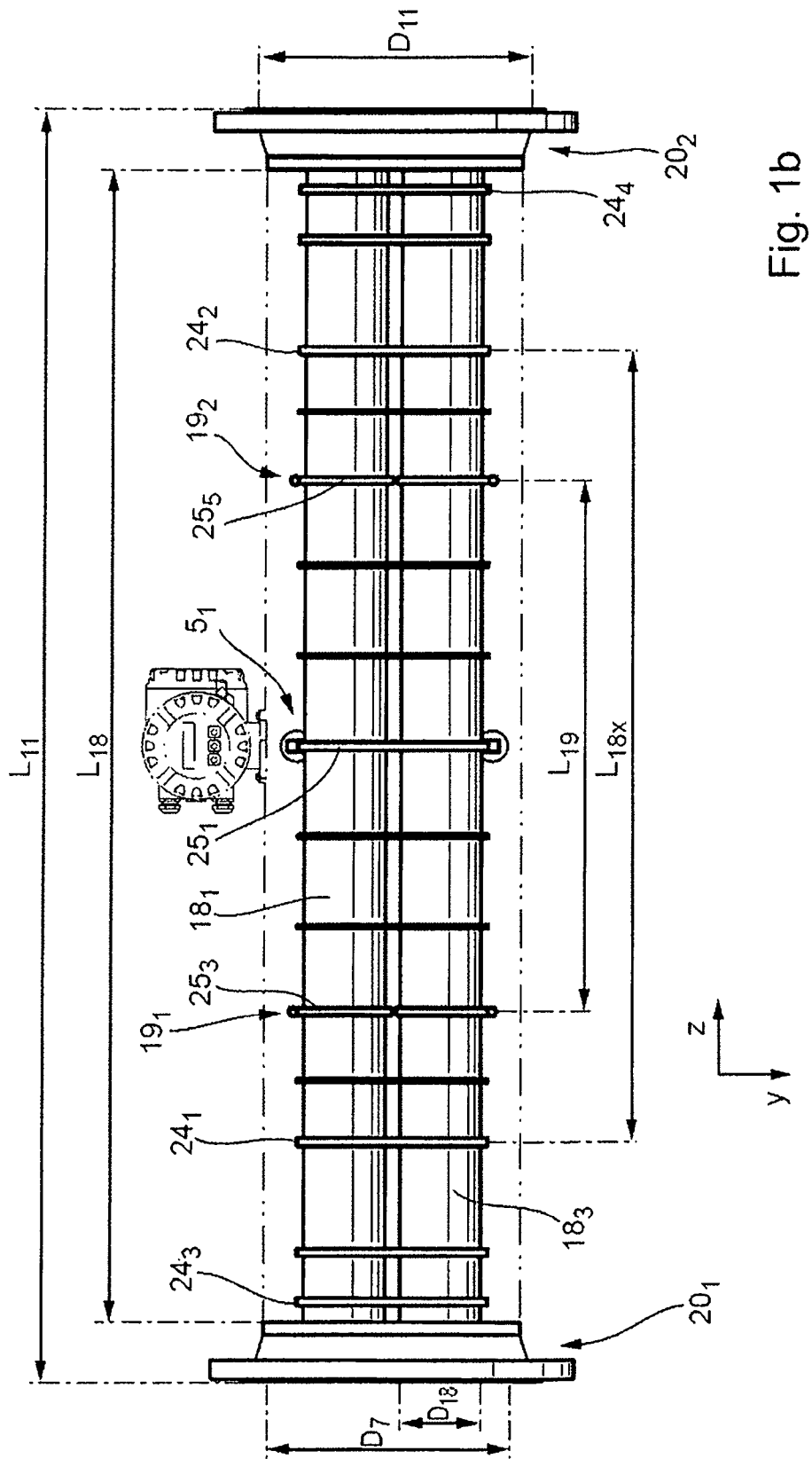
Figure 1C:
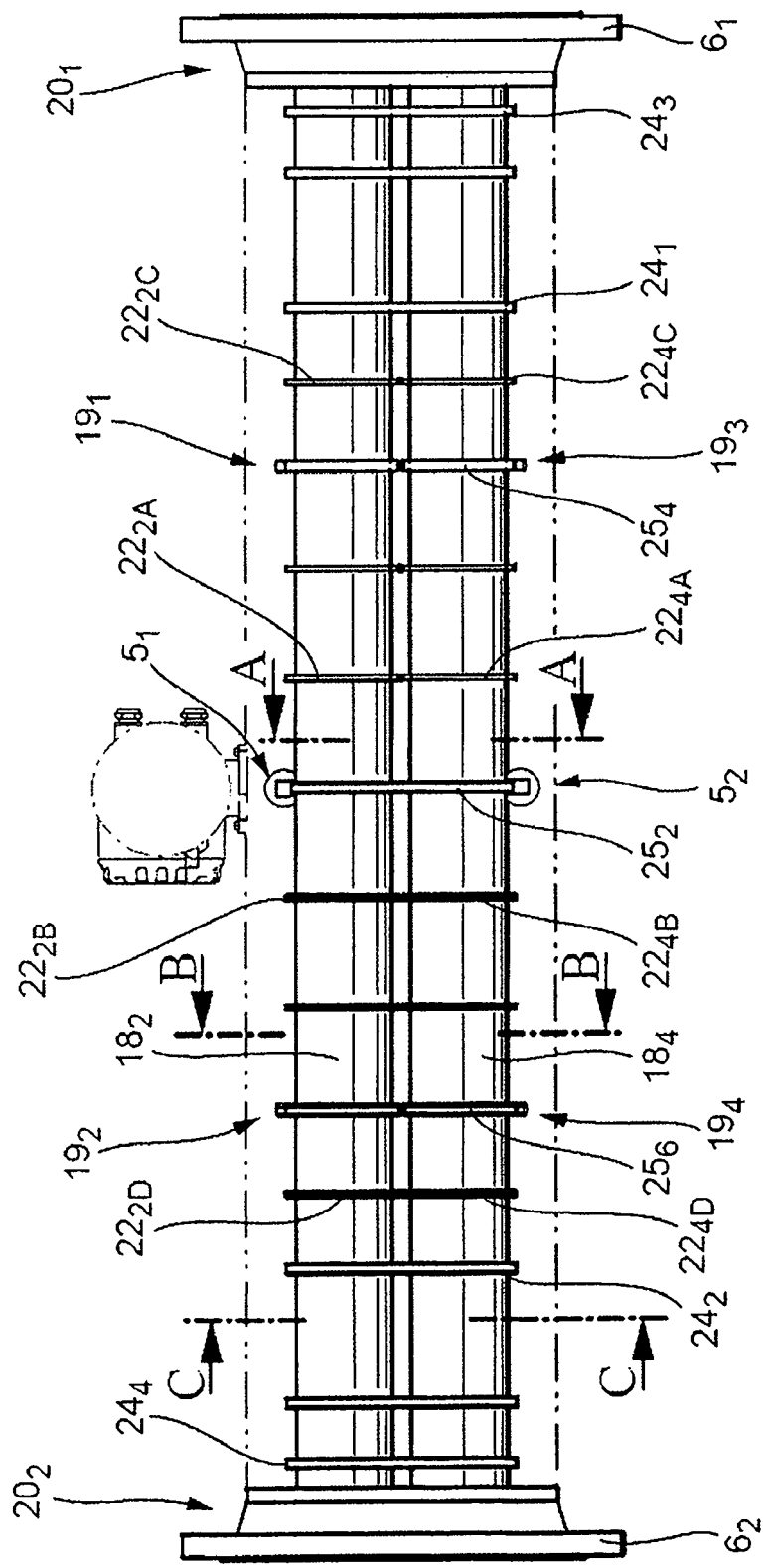
Figure 2:
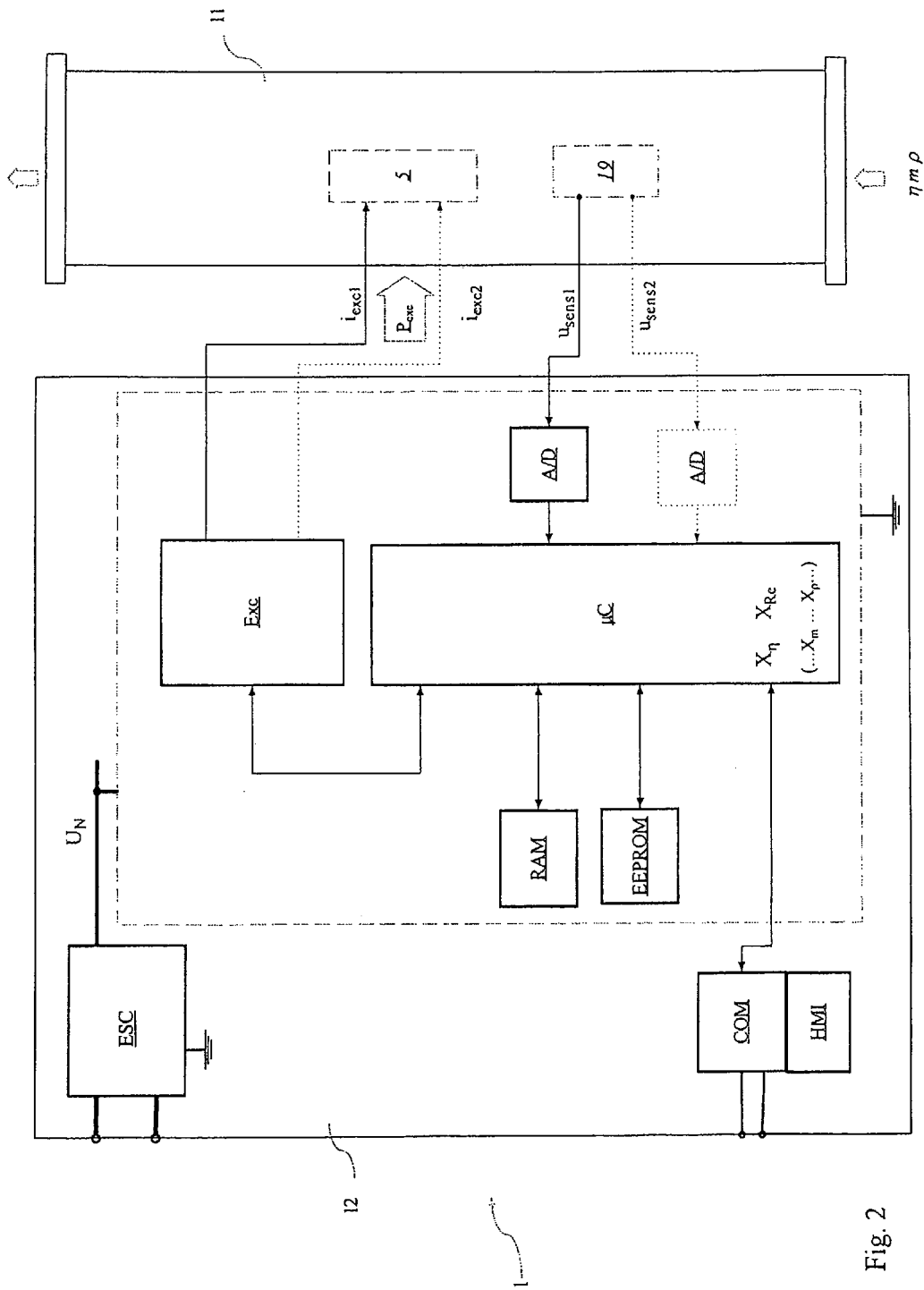
FIG. 2 schematically in the manner of a block diagram, a transmitter electronics, to which is connected a measuring transducer of vibration-type for forming a measuring system according to FIG. 1.
Figure 3:
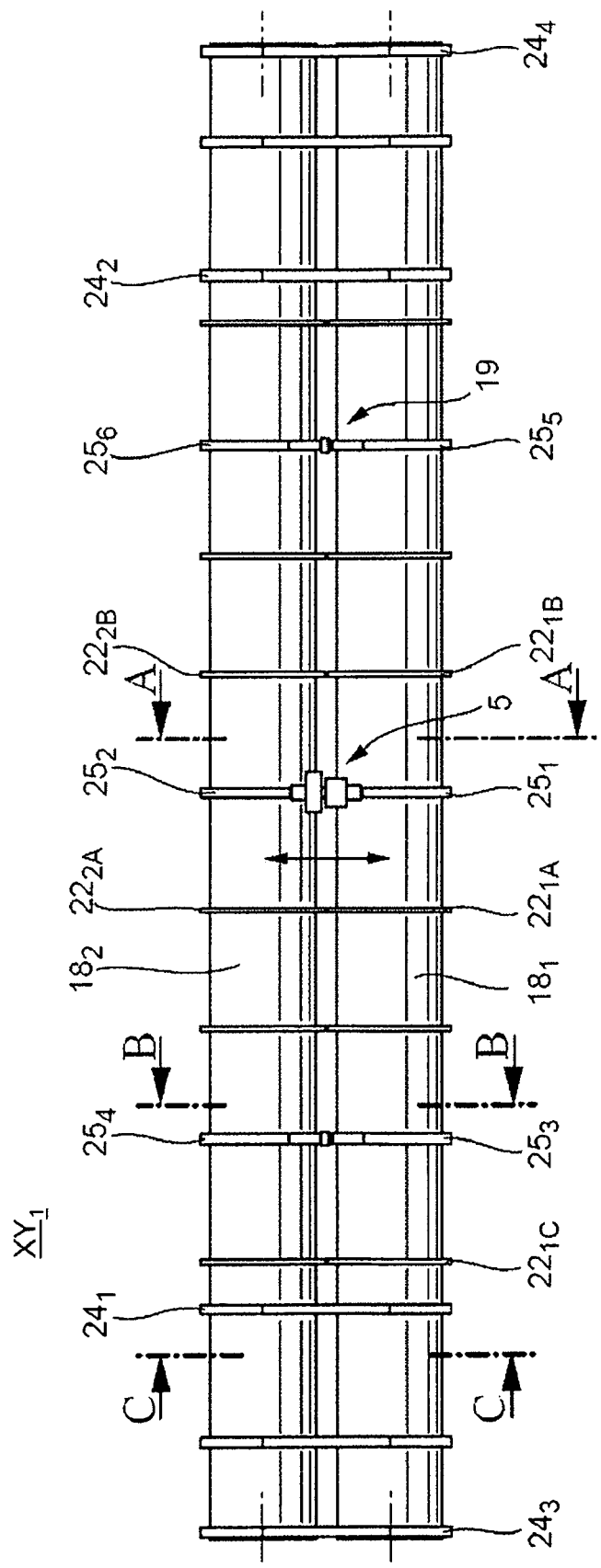
FIG. 3 in, partially sectioned, or perspective, side views, an example of an embodiment of a measuring transducer of vibration-type, especially one suited for a measuring system according to FIG. 1, or 2.
Figure 4:
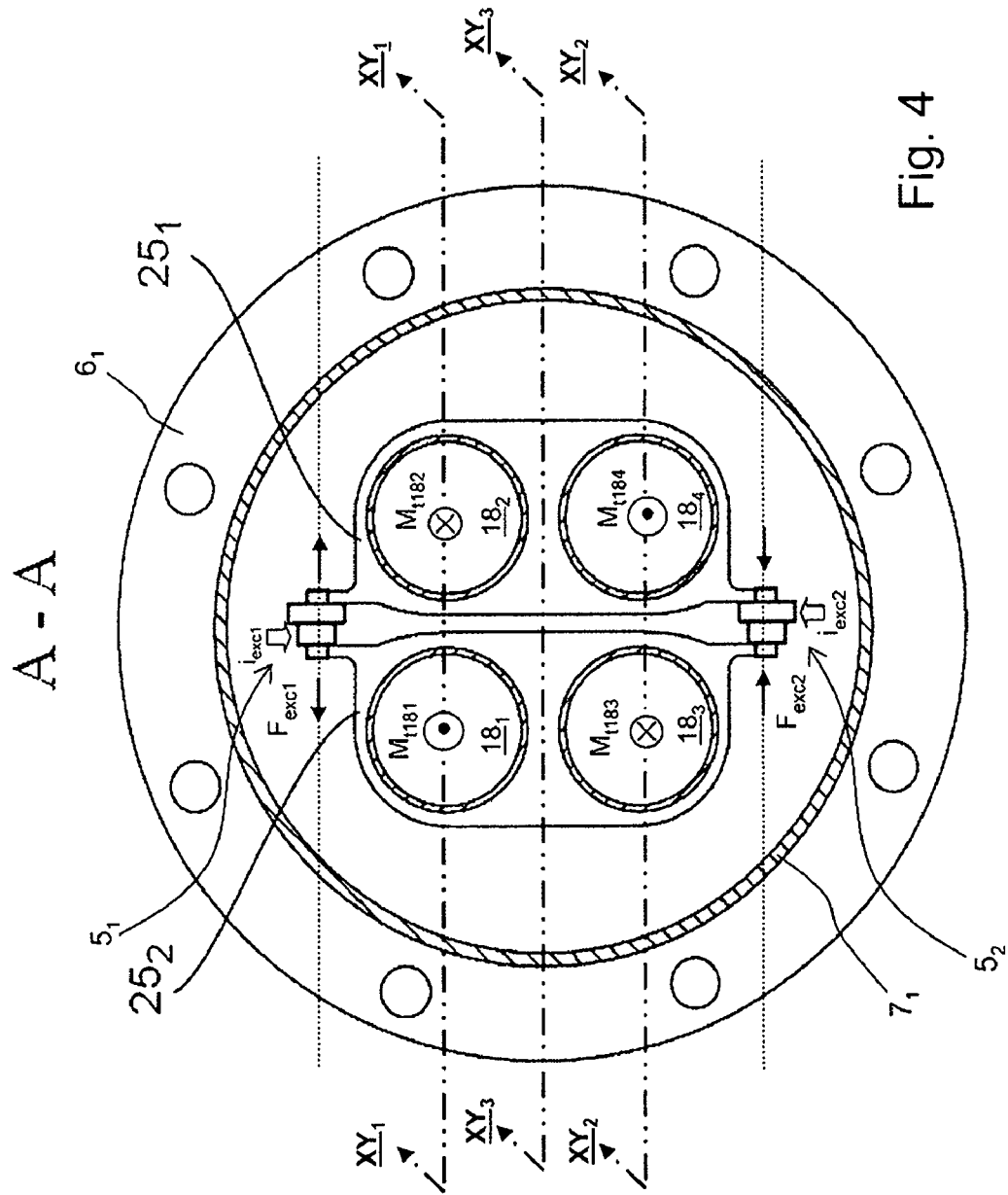
FIG. 4, FIG. 5 and FIG. 6 projections of a tube arrangement of the measuring transducer according to FIG. 3 in different side views.
Figure 5:
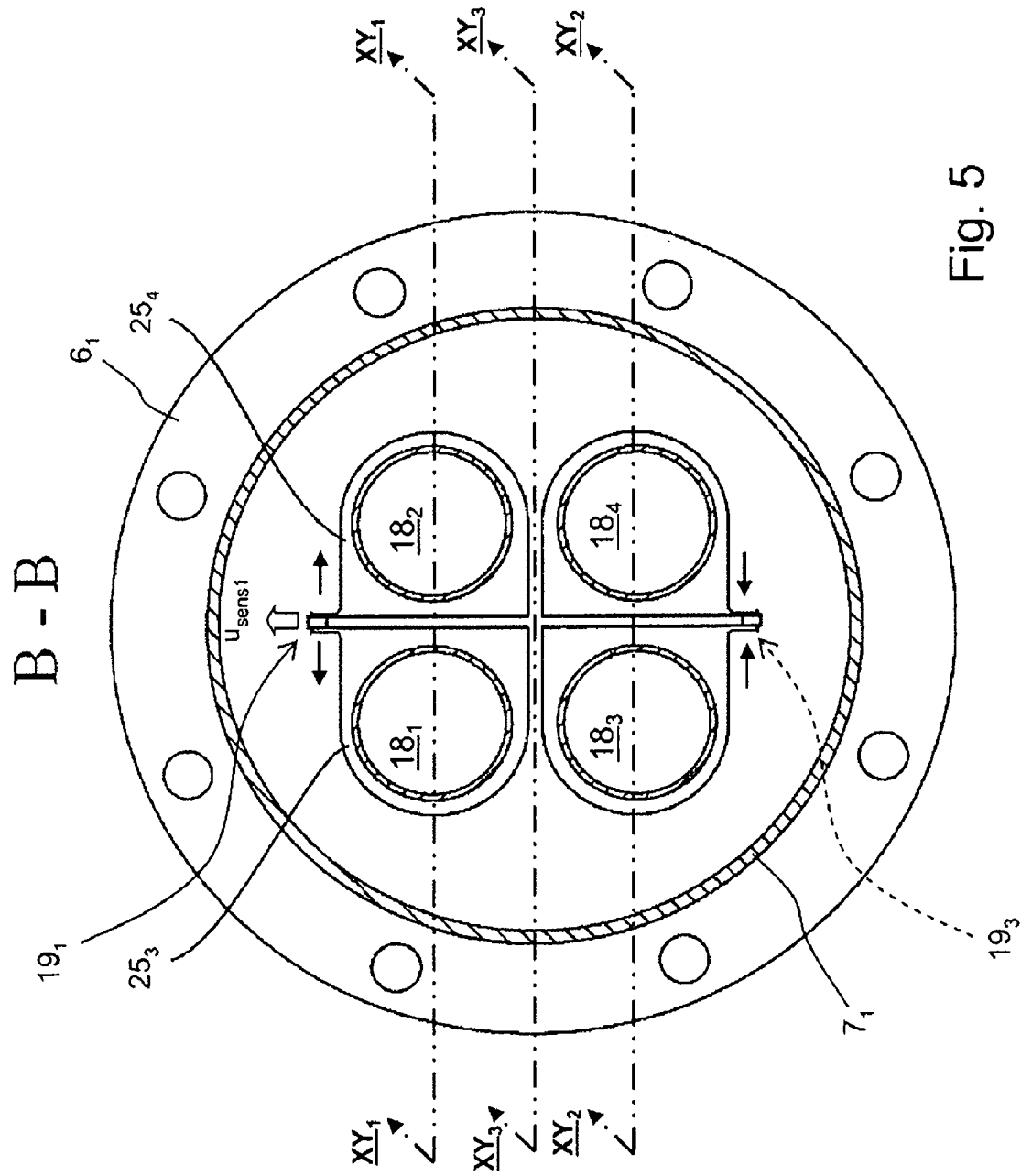
Figure 6:
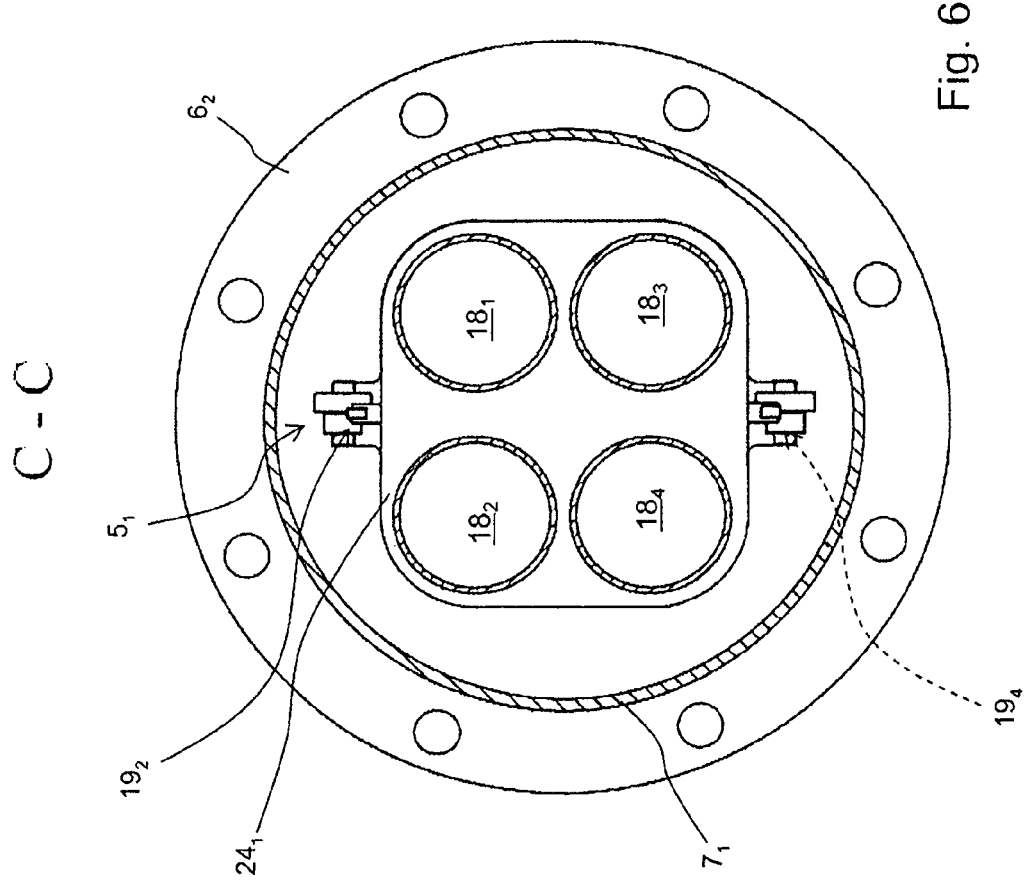

The transmitter electronics 12 includes, as shown in FIG. 2 schematically in the manner of a block diagram: A driver circuit Exc serving for driven the measuring transducer; as well as a measuring, and evaluating, circuit µC processing primary signals of the measuring transducer 11, for example, formed by means of a microcomputer and/or communicating during operation with the driver circuit Exc. During operation, the measuring, and evaluating, circuit µC delivers measured values representing the at least one measured variable, such as e.g. the viscosity and/or the Reynolds number, as well as, in given cases, other measured variables, such as the density and/or the instantaneous, or a totaled, mass flow of the flowing medium. The driver circuit Exc and the evaluating circuit µC, as well as other electronics components of the transmitter electronics serving the operation of the measuring system, such as, for instance, internal energy supply circuits ESC for providing internal supply voltages $U_N$ and/or communication circuits COM serving for connection to a superordinated measurement data processing system and/or a fieldbus, are, in the here illustrated example of an embodiment, additionally accommodated in a—here single, especially impact and/or also explosion resistantly and/or hermetically sealed—electronics housing $7_2$. For visualizing measuring system internally produced, measured values and/or, in given cases, measuring system internally generated, status reports, such as, for instance, an error report or an alarm, onsite, the measuring system can, furthermore, have a display, and interactions, element HMI communicating, at least at times, with the transmitter electronics, such as, for instance, a LCD-, OLED- or TFT-display placed in the electronics housing behind a window correspondingly provided therein as well as a corresponding input keypad and/or a touch-screen. In advantageous manner, the, for example, (re-) programmable and/or remotely parameterable, transmitter electronics 12 can additionally be so designed, that it can during operation of the inline measuring device exchange with a electronic data processing system superordinated thereto, for example, a programmable logic controller (PLC), a personal computer and/or a work station, via a data transmission system, for example, a fieldbus system and/or wirelessly per radio, measuring—and/or other operating data, such as, for instance, current measured values or tuning—and/or diagnostic values serving the control of the inline measuring device. In such case, the transmitter electronics 12 can have, for example, an internal energy supply circuit ESC, which is fed during operation via the aforementioned fieldbus system from an external energy supply provided in the data processing system. In an embodiment of the invention, the transmitter electronics is additionally so embodied, that it is connectable electrically with the external electronic data processing system by means of a two-wire connection 2L configured, for example, as a 4-20 mA-current loop, and can transmit thereby, measured values to the data processing system, as well as being, in given cases, also supplied—at least partially or exclusively—with electrical energy thereby. For the case, in which the measuring system is to have the capability for a coupling to a fieldbus—or other communication system, the transmitter electronics 12 can have a corresponding communication interface COM for data communication according to one of the relevant industry standards.

In FIGS. 3, 4, 5, and 6, there is shown, supplementary to, respectively, FIGS. 1a, 1b, 1c, and 2, in different representations, a measuring transducer 11 suited for reducing the measuring system of the invention to practice, in given cases, also applicable for mass flow—and/or density measuring. This measuring transducer 11 is inserted during operation in the course of a pipeline (not shown), through which medium to be measured flows. The measuring transducer 11 serves, as already mentioned, to produce in a through flowing medium mechanical reaction forces, especially also frictional forces dependent on the viscosity of the medium, in given cases, also Coriolis forces dependent on the mass flow and/or inertial forces dependent on the density of the medium, which react measurably, especially registerably by sensor, on the measuring transducer, and to convert such into primary signals—here embodied as oscillatory signals—corresponding therewith. Based on these reaction forces describing the flowing medium, or the therefrom derived, primary signals of the measuring transducer, e.g. the viscosity $\eta$ of the medium, the mass flow, the density and/or therefrom derived measured variables, such as, for instance, the Reynolds number Re can be measured by means of evaluating methods correspondingly implemented in the transmitter electronics.

The measuring transducer 11 includes—as directly evident from the combined figures—a transducer housing $7_1$—here essentially tubular, and outwardly circularly cylindrical in form—serving, among other things, also as a support frame. In the housing, other components of the measuring transducer 11 serving the registering of the at least one measured variable are accommodated protected against external, environmental influences. In the example of an embodiment shown here, at least a middle segment of the transducer housing $7_1$ is formed by means of a straight, especially circularly cylindrical, tube, so that, for the manufacture of the transducer housing, for example, also cost effective, welded or cast, standard tubes, for example, of cast steel or forged steel, can be used. An inlet-side, first housing end of the transducer housing $7_1$ is formed by means of an inlet-side, first flow divider $20_1$ and an outlet-side, second housing end of the transducer housing $7_1$ by means of an outlet-side, second flow divider $20_2$. Each of the two flow dividers $20_1$, $20_2$, thus formed as integral components of the housing, includes in the here illustrated example of an embodiment exactly two flow openings $20_{1A}$, $20_{1B}$, and $20_{2A}$, $20_{2B}$, respectively, in each case, spaced from one another, and embodied, for example, circularly cylindrically or conically, or, in each case, as inner cones. Moreover, each of the flow dividers $20_1$, $20_2$, manufactured, for example, from steel, is provided with a flange $6_1$, or $6_2$, for example, of steel, for connecting the measuring transducer 11 to a tube segment of the pipeline serving for supplying medium to the measuring transducer, or to a tube segment of the mentioned pipeline serving for removing medium from the measuring transducer. For leakage free, especially fluid tight, connecting of the measuring transducer with the, in each case, corresponding tube segment of the pipeline, each of the flanges includes additionally, a corresponding sealing surface $6_{1A}$, or $6_{2A}$, each of which is as planar as possible. A distance between the two sealing surfaces $6_{1A}$, $6_{2A}$ of the two flanges defines, thus, for practical purposes, an installed length, $L_{11}$, of the measuring transducer 11. The flanges are, especially as regards their inner diameter, their respective sealing surfaces as well as the flange bores serving for accommodating corresponding connection bolts, dimensioned corresponding to the nominal diameter $D_{11}$ provided for the measuring transducer 11 as well as the, in given cases, relevant industrial standards appropriate for a caliber of the pipeline, in whose course the measuring transducer is to be used. As a result of the rather large nominal diameter of 100 mm or thereover ultimately desired for the measuring transducer, its installed length $L_{11}$ amounts according to an embodiment of the invention to more than 800 mm. Additionally, it is, however, provided that the installed length of the measuring transducer 11 is kept as small as possible, especially smaller than 3000 mm. The flanges $6_1$, $6_2$ can, as well as also directly evident from, respectively, FIGS. 1a, 1b, and 1c and as quite usual in the case of such measuring transducers, be arranged therefor as near as possible to the flow openings of the flow dividers $20_1$, $20_2$, in order to so provide an as short as possible in—, or outlet region in the flow dividers and, thus, as a whole, to provide an as short as possible installed length $L_{11}$ the measuring transducer, especially less than 3000 mm. For an as compact as possible measuring transducer also combined with desired high mass flow rates of over 1200 t/h, according to another embodiment of the invention, the installed length and the nominal diameter of the measuring transducer are so dimensioned matched to one another, that a nominal diameter to installed length ratio $D_{11}/L_{11}$ the measuring transducer, defined by a ratio of the nominal diameter $D_{11}$ the measuring transducer to the installed length $L_{11}$ the measuring transducer is smaller than 0.3, especially smaller than 0.2 and/or greater than 0.1. In an additional embodiment of the measuring transducer, the transducer housing has an essentially tubular, middle segment. Additionally, it is provided to so dimension the transducer housing, that a housing inner diameter to nominal diameter ratio of the measuring transducer defined by a ratio of the largest housing inner diameter to the nominal diameter of the measuring transducer is, indeed, greater than 0.9, however, smaller than 1.5, as much as possible, however, smaller than 1.2.

In the case of the here illustrated example of an embodiment, there adjoin on the middle segment on the inlet side and on the outlet side, respectively, additionally likewise tubular end segments of the transducer housing. For the case illustrated in the example of an embodiment, wherein the middle segment and the two end segments, as well as also the respective flange-connected flow dividers in the inlet and outlet regions, respectively, in each case, have the same inner diameter, the transducer housing can in advantageous manner also be formed by means of a one piece, for example, cast or forged, tube, on whose ends the flanges are formed or welded on, and wherein the flow dividers are formed by means of plates, especially plates somewhat spaced from the flanges, welded orbitally on the inner wall and/or welded-on by means of laser, and having the flow openings. Especially, for the case, in which the mentioned housing inner diameter to nominal diameter ratio of the measuring transducer is selected equal to one, for manufacture of the transducer housing, for example, a tube corresponding to the pipeline to be connected to as regards caliber, wall thickness and material and, insofar, also correspondingly adapted as regards the allowed operating pressure, with length correspondingly matching the selected measuring tube length can be used. For simplifying the transport of the measuring transducer, or the total therewith formed, inline measuring device, additionally, as, for example, also provided in the initially mentioned U.S. Pat.

No. 7,350,421, a transport eye can be provided, affixed on the inlet side and on the outlet side on the exterior of the transducer housing.

For conveying the medium flowing, at least at times, through pipeline and measuring transducer, the measuring transducer of the invention comprises additionally at least four (in the here illustrated example of an embodiment, exactly four), mutually parallel, straight, measuring tubes $18_1$, $18_2$ held oscillatably in the transducer housing 10. During operation, measuring tubes $18_1$, $18_2$, in each case, communicate with the pipeline and are, at least at times, actively excited and caused to vibrate in at least one oscillatory mode suited for ascertaining the physical, measured variable, the so-called driven, or also wanted, mode. Of the at least four—here essentially circularly cylindrical, and to one another as well as to the above mentioned middle tube segment of the transducer housing, in each case parallel—measuring tubes, a first measuring tube $18_1$ opens with an inlet-side, first measuring tube end into a first flow opening $20_{1A}$ of the first flow divider $20_1$ and with an outlet-side, second measuring tube end into a first flow opening $20_{2A}$ of the second flow divider $20_2$ and a second measuring tube $18_2$ opens with an inlet-side, first measuring tube end into a second flow opening $20_{1B}$ of the first flow divider $20_1$ and with an outlet-side, second measuring tube end into a second flow opening $20_{2B}$ of the second flow divider $20_2$, a third measuring tube $18_3$ opens with an inlet-side, first measuring tube end into a third flow opening $20_{1C}$ of the first flow divider $20_1$ and with an outlet-side, second measuring tube end into a third flow opening $20_{2C}$ of the second flow divider $20_2$ and a fourth measuring tube $18_4$ opens with an inlet-side, first measuring tube end into a fourth flow opening $20_{1D}$ of the first flow divider $20_1$ and with an outlet-side, second measuring tube end into a fourth flow opening $20_{2D}$ of the second flow divider $20_2$.

The measuring tubes $18_1$, $18_2$, $18_3$, $18_4$ are, thus, connected to the flow dividers $20_1$, $20_2$, especially equally-constructed, flow dividers, for forming a tube arrangement with at least four parallel flow paths and, indeed, in a manner enabling vibrations, especially bending oscillations, of the measuring tubes relative to one another, as well as also relatively to the transducer housing. In the case of the measuring system of the invention, said tube arrangement is additionally so embodied, that it has both a first imaginary longitudinal section plane, in which extend both a measuring tube, longitudinal axis of the first measuring tube, which imaginarily connects its first and second measuring tube ends, as well as also a measuring tube, longitudinal axis of the second measuring tube, which imaginarily connects its first and second measuring tube ends and is parallel to the measuring tube, longitudinal axis of the first measuring tube, as well as also, spaced from the first imaginary longitudinal section plane and parallel thereto, a second imaginary longitudinal section plane, in which extend both a measuring tube, longitudinal axis of the third measuring tube, which imaginarily connects its first and second measuring tube ends, as well as also a measuring tube, longitudinal axis of the fourth measuring tube, which imaginarily connects its first and second measuring tube ends and is parallel to the measuring tube, longitudinal axis of the first measuring tube, as well as, between the first longitudinal section plane $XZ_1$ and second longitudinal section plane $XZ_2$, in each case, spaced from the first imaginary longitudinal section plane and from the second imaginary longitudinal section plane and, in each case, parallel to the first and second longitudinal section planes, a third imaginary longitudinal section plane $XZ_3$.

Especially, it is additionally provided, that the measuring tubes $18_1$, $18_2$, $18_3$, $18_4$ as quite usual in the case of such measuring transducers, are held oscillatably only by means of said flow dividers $20_1$, $20_2$ in the transducer housing $7_1$, thus—apart from the electrical connecting lines—there are otherwise no other mentionable mechanical connections to the transducer housing with has. Moreover, the first measuring tube has, according to an additional embodiment of the invention, a caliber, which equals a caliber of the second measuring tube, for example, also in such a manner, that all four measuring tubes are of equal caliber.

The measuring tubes $18_1$, $18_2$, $18_3$, $18_4$, or the therewith formed, tube arrangement of the measuring transducer 11, are, as certainly also directly evident from the combination of FIGS. 1, 3, 4 and 5, and as also usual in the case of such measuring transducers, encased by the transducer housing $7_1$, in the illustrated instance, practically completely encased. The transducer housing $7_1$ serves, thus not only as support frame or holder of the measuring tubes $18_1$, $18_2$, $18_3$, $18_4$ but, instead, moreover, also to protect these, as well as also other components placed within the transducer housing $7_1$ of the measuring transducer, against outer, environmental influences, such as e.g. dust or water spray. Moreover, the transducer housing $7_1$ can additionally also be so executed and so dimensioned, that, it in the case of possible damage to one or more of the measuring tubes, e.g. through crack formation or bursting, outflowing medium can be completely retained up to a required maximum positive pressure in the interior of the transducer housing $7_1$ for as long as possible, wherein such critical state can, as, for example, mentioned also in the initially cited U.S. Pat. No. 7,392,709, be registered and signaled by means of corresponding pressure sensors and/or on the basis of operating parameters internally produced by the mentioned transmitter electronics during operation. Accordingly, used as material for the transducer housing $7_1$ can be, especially, steels, such as, for instance, structural steel, or stainless steel, or also other suitable high strength materials, or high strength materials usually suitable for this.

Suitable as material for the tube walls of the measuring tubes—here, equally large measuring tubes, are, again, especially, titanium, zirconium or tantalum. Moreover, serving as material for the measuring tubes $18_1$, $18_2$, $18_3$, $18_4$ can be, however, also practically any other, usually applied therefor or at least suitable, material, especially such having an as small as possible thermal expansion coefficient and an as high as possible yield point. For most applications of industrial measurements technology, especially also in the petrochemicals industry, consequently, also measuring tubes of stainless steel, for example, also duplex steel or super duplex steel, would satisfy the requirements as regards mechanical strength, chemical resistance as well as thermal requirements, so that, in numerous cases of application, the transducer housing $7_1$, the flow dividers $20_1$, $20_2$, as well as also the tube walls of the measuring tubes $18_1$, $18_2$, $18_3$, $18_4$, in each case, can be of steel of, in each case, sufficiently high quality, which can be of advantage, especially as regards material—and manufacturing costs, as well as also the thermally related dilation behavior of the measuring transducer 11 during operation. According to an embodiment, the measuring tubes $18_1$, $18_2$, $18_3$, $18_4$ of the invention are in advantageous manner additionally so embodied and so installed in the measuring transducer 11, that at least the minimum torsional oscillation, resonance frequencies $f_t 18_1$, $f_t 18_2$ of the first and second measuring tubes $18_1$, $18_2$ are essentially equal to one another. Furthermore, it can be of advantage additionally to so construct and to so install the measuring tubes $18_1$, $18_2$ in the measuring transducer 11, that at least also the minimum bending oscillation, resonance frequencies $f_b 18_1$, $f_b 18_2$ of the first and second measuring tubes $18_1$, $18_2$ are essentially equal to one another. Furthermore, the tube arrangement is additionally so embodied, that at least one eigen—or resonance frequency of natural bending oscillations of the first measuring tube, for example, such in a bending oscillation, fundamental mode having a single oscillatory antinode, equals an eigenfrequency of natural torsional oscillations of the first measuring tube, for example, such in a torsional oscillation, fundamental mode having a single oscillatory antinode, and that at least one eigenfrequency of natural bending oscillations of the second measuring tube, for instance, such in a bending oscillation, fundamental mode having a single oscillatory antinode, equals an eigenfrequency of natural torsional oscillations of the second measuring tube, for instance, such in a torsional oscillation, fundamental mode having a single oscillatory antinode.

As already mentioned, in the case of the measuring transducer 11, the reaction forces required for the measuring, especially the measuring of viscosity and/or Reynolds number of the flowing medium, are effected in the medium to be measured by causing the measuring tubes $18_1$, $18_2$, $18_3$, $18_4$ to oscillate in the so-called wanted, or driven, mode. In the case of the measuring system of the invention, selected as wanted mode is an oscillatory mode wherein each of the measuring tubes $18_1$, $18_2$, $18_3$, $18_4$ executes, at least partially, torsional oscillations about an, in each case, associated imaginary measuring tube longitudinal axis imaginarily connecting its particular measuring tube ends, for example, with a respective natural, torsional oscillation, resonance frequency intrinsic to the respective measuring tube.

For exciting mechanical oscillations of the tube arrangement, thus, of torsion—or torsion/bending oscillations of the measuring tubes $18_1$, $18_2$, $18_3$, $18_4$, the measuring transducer includes additionally an exciter mechanism 5 formed by means of at least a first, electromechanical, for example, electrodynamic, oscillation exciter acting—, for example, differentially—on at least the measuring tubes $18_1$, $18_2$, in given cases also simultaneously on the third and fourth measuring tubes and by means of a second, electromechanical, for example, electrodynamic, oscillation exciter acting—, for example, differentially—on at least the measuring tubes $18_3$, $18_4$, in given cases also simultaneously on the first and second measuring tubes and serving to cause each of the measuring tubes operationally, at least at times, to execute suitable mechanical oscillations in the wanted mode—namely, for example, torsional oscillations with a minimum torsional oscillation resonance frequency of the measuring tubes, and/or torsion/bending oscillations—with, in each case, sufficiently large oscillation amplitude for producing and registering the above named reaction forces in the medium, and, respectively, to maintain said oscillations. The aforementioned torsion/bending oscillations can, for example, be coupled oscillations, thus oscillations of equal frequency and standing in fixed phase relationship to one another or, however, also simultaneously, or intermittently, executed torsion—and bending oscillations with different torsion—and bending oscillation frequencies. In accordance therewith, according to an additional embodiment of the invention; the exciter mechanism is designed also to effect, thus, actively to excite (in given cases, also simultaneously to the mentioned torsional oscillations of each of the measuring tubes $18_1$, $18_2$, $18_3$, $18_4$) both bending oscillations of the first measuring tube about its measuring tube, longitudinal axis and bending oscillations of the second measuring tube about its measuring tube, longitudinal axis opposite-equal to the bending oscillations of the first measuring tube, as well as also bending oscillations of the third measuring tube about its measuring tube, longitudinal axis and bending oscillations of the fourth measuring tube about its measuring tube, longitudinal axis and opposite-equal to the bending oscillations of the third measuring tube.

The first oscillation exciter of the exciter mechanism serves, in such case, correspondingly to convert an electrical excitation power $P_{exc}$, fed into the exciter mechanism by the transmitter electronics by means of a first electrical driver signal $i_{exc1}$ supplied to the exciter mechanism, particularly also a power dependent on a voltage level and an electrical current level of the first driver signal $i_{exc1}$, namely into corresponding periodic, in given cases, also harmonic, exciter forces $F_{exc1}$, which act as simultaneously and uniformly as possible, however, with opposite sense, on the first and second measuring tubes $18_1$, $18_2$, in given cases, additionally also on the third and fourth measuring tube. Moreover, the second oscillation exciter, for example, an electrodynamic second oscillation exciter, or a second oscillation exciter constructed equally to the first oscillation exciter, serves particularly to convert electrical excitation power fed into the exciter mechanism, for example, also by means of the first electrical driver signal iexc1, into mechanical exciter forces Fexc2 effecting the simultaneous torsional oscillations of the four measuring tubes.

In the case of the measuring system of the invention, the exciter mechanism formed by means of at least two oscillation exciters—here oscillation exciters placed, respectively, above and below the mentioned third imaginary longitudinal section plane of the tube arrangement, for example, essentially equally constructed, oscillation exciters—is, especially, so embodied, that it converts the fed electrical excitation power, as already indicated, at least at times, and/or at least partially, into both torsional oscillations of the first measuring tube $18_1$ and thereto opposite-equal torsional oscillations of the second measuring tube $18_2$ as well as also into torsional oscillations of the third measuring tube $18_1$ and torsional oscillations of the fourth measuring tube $18_4$ opposite-equal to the torsional oscillations of the third measuring tube $18_3$ (in the excited—or wanted mode).

Additionally, it is provided, according to an embodiment of the invention, that the first oscillation exciter is constructed as an oscillation exciter acting differentially on the first and second measuring tubes, namely that the exciter mechanism effects oscillations of the measuring tubes, thus, opposite-equal torsional oscillations of the first and second measuring tubes or opposite-equal bending/torsional oscillations of the first and second measuring tubes, by the feature that an exciter force generated by means of the first oscillation exciter 51, acting on the first measuring tube, is opposite, especially opposite-equal, to an exciter force generated at the same time by means of the first oscillation exciter, acting on the second measuring tube. Additionally, the exciter mechanism and the at least one driver signal $i_{exc1}$ can, in such case, in advantageous manner, be embodied in such a manner and so matched to one another, that therewith the first measuring tube $18_1$ and the second measuring tube $18_2$ are excited during operation, at least at times,—for example, also simultaneously with the torsional oscillations—to opposite phase bending oscillations about the particular, imaginary measuring tube, longitudinal axis. In supplementation thereof, the first oscillation exciter is additionally embodied as an oscillation exciter of electrodynamic type. In accordance therewith, the oscillation exciter 51 includes, in the case of this embodiment, a permanent magnet held on the first measuring tube $18_1$ and a cylindrical coil held on the second measuring tube $18_2$ and permeated by the magnetic field of the permanent magnet; especially, the oscillation exciter 51 is embodied as a type of coil, plunger arrangement, in the case of which the cylindrical coil is arranged coaxially to the permanent magnet and the permanent magnet is embodied as a plunging armature moved within said cylindrical coil. Additionally, it is, in such case, provided, that the first driver signal $i_{exc1}$ is fed to the first oscillation exciter 51, or, in said oscillation exciter 51, electrical excitation power correspondingly to be converted therein is fed in, in that a first exciter current flows through the cylindrical coil of the oscillation exciter 51 driven by a variable first exciter voltage provided by means of the driver signal.

In an additional embodiment of the invention, the first oscillation exciter 51 is further so embodied and placed on the tube arrangement, that the therewith produced—here essentially translational—exciter forces $F_{exc1}$ are introduced along an imaginary line of action into the tube arrangement spaced from the mentioned third imaginary longitudinal section plane—here also from the first and second imaginary longitudinal section planes—and, apart from a principle of action related slight curvature and a component tolerance related, slight offset, extending at least approximately parallel thereto, for example, also essentially transversely to the measuring tube, longitudinal axis of the first measuring tube and to the measuring tube, longitudinal axis of the second measuring tube, and, as a result, there can be produced in each of the measuring tubes corresponding torsional moments $M_t18_1$, $M_t18_2$ about the associated measuring tube, longitudinal axes. Especially, the first oscillation exciter $5_1$ is, in such case, so embodied and arranged in the measuring transducer, that the line of action, with which the exciter forces produced by the first oscillation exciter are introduced into the tube arrangement, has a perpendicular distance to the third imaginary longitudinal section plane of the tube arrangement, which is greater than three fourths of the caliber of the first measuring tube, especially greater than 100% of the first measuring tube, and/or smaller than 200% of the caliber of the first measuring tube, for example, also smaller than 150% of the caliber of the first measuring tube. As a result of this, the first oscillation exciter, as directly evident from the combination of FIGS. 1a, 1b, 1c, 3 and 4, is thus placed on a side, here the upper side, facing away from the second oscillation exciter 52 of the third imaginary longitudinal section plane $XZ_3$ of the tube arrangement in the measuring transducer, and, indeed, in the here illustrated example of an embodiment, also on a side, here the upper side, facing away from the second oscillation exciter 51 of the first imaginary longitudinal section plane $XZ_1$ of the tube arrangement.

In another embodiment of the invention, the second oscillation exciter, particularly also for increasing the robustness and stability, with which the oscillations are actually excited in the wanted mode and/or for the purpose of exciting, simultaneously or alternatively, of torsional, and bending, oscillations in each of the measuring tubes, is further so embodied and placed on the tube arrangement, that the therewith produced exciter forces $F_{exc2}$ are introduced along an imaginary line of action into the tube arrangement spaced from the mentioned third imaginary longitudinal section plane $XZ_3$ and extending at least approximately parallel thereto, for example, also essentially transversely to the measuring tube, longitudinal axis of the third measuring tube and to the measuring tube, longitudinal axis of the fourth measuring tube, and, as a result, there can be produced in the third and fourth measuring tubes corresponding torsional moments $M_t18_3$, $M_t18_4$ about the associated measuring tube, longitudinal axis. As directly evident from the combination of FIGS. 1a, 1b, 1c, 3 and 4, the second oscillation exciter $5_2$ for this is placed in the measuring transducer on a side, here the lower side, of the third imaginary longitudinal section plane $XZ_3$ of the tube arrangement facing away from the first oscillation exciter 51, here additionally also on a side, here the lower side of the second imaginary longitudinal section plane $XZ_2$ of the tube arrangement facing away from the first oscillation exciter 51. Especially, the first oscillation exciter 51 and the second oscillation exciter 52 are, according to an additional embodiment, additionally so embodied and arranged in the measuring transducer, that, as directly evident from the combination of FIGS. 1 and 4, the line of action, with which the exciter forces produced by the first oscillation exciter are introduced into the tube arrangement, has a perpendicular distance to the third imaginary longitudinal section plane of the tube arrangement, which is greater than three fourths of the caliber of the first measuring tube, especially greater than 100% of the caliber of the first measuring tube, and/or smaller than 200% of the caliber of the first measuring tube, especially, also in the order of magnitude of 150% of said caliber. In the example of an embodiment shown here, the two oscillation exciter 51, 52 are additionally so placed in the measuring transducer, that the first oscillation exciter arranged above the first imaginary longitudinal section plane $XZ_1$ of the tube arrangement and the second oscillation exciter arranged below the second imaginary longitudinal section plane $XZ_2$ are positioned, in each case, in equal distance to the third imaginary longitudinal section plane $XZ_3$, consequently also equidistant to a center of mass of the tube arrangement. For producing differently large torsional moments—, for example, also for the purpose of exciting of coupled torsion/bending oscillations—the two oscillation exciters can, however, also be placed with different distances to the center of mass of the tube arrangement, or to the third imaginary longitudinal section plane $XZ_3$.

Particularly also for the purpose of implementing the aforementioned spacing of the respective oscillation exciter from, in each case, the measuring tubes, especially also a spacing serving for the conversion of essentially translational exciter forces produced on the part of the at least one oscillation exciter into corresponding torsional moments, as well as also for the purpose of transfer of the exciter forces produced on the part of the first oscillation exciter also onto the third and fourth measuring tubes, or the exciter forces produced on the part of the second oscillation exciter onto the first and second measuring tubes, the measuring transducer, according to an additional embodiment of the invention, comprises additionally a first coupling element $25_1$ of first type affixed both to the first measuring tube as well as also to the third measuring tube, but otherwise to no other measuring tube, for example, an essentially plate shaped, first coupling element $25_1$ of first type, for holding components of the first oscillation exciter, for example, a cylindrical coil or a permanent magnet, and for introducing an exciter force generated by means of the first oscillation exciter into the first measuring tube and/or for converting an exciter force generated by means of the first oscillation exciter into a torsional moment $Mt18_1$ acting on the first measuring tube and a torsional moment $Mt18_3$ acting on the third measuring tube, as well as a second coupling element $25_1$ of first type affixed both to the second measuring tube as well as also to the third measuring tube, but otherwise to no other measuring tube, for example, an essentially plate shaped, second coupling element $25_1$ of first type and/or a second coupling element $25_1$ of first type constructed equally to the first coupling element $25_1$ of first type, for holding components of the first oscillation exciter, for example, thus a cylindrical coil, or a permanent magnet, and for introducing an exciter force generated by means of the first oscillation exciter into the second measuring tube and/or for converting an exciter force generated by means of the first oscillation exciter into a torsional moment $Mt18_2$ acting on the second measuring tube and a torsional moment $Mt18_4$ acting on the fourth measuring tube. As directly evident from the combination of FIGS. 1a, 1b, 1c, 3 and 4, the first and second coupling elements $25_1$, $25_2$ of first type are as much as possible oppositely lying to one another, however, placed spaced from one another in the measuring transducer 11 in a manner enabling relative oscillatory movements of the measuring tubes. Furthermore, in the here illustrated example of an embodiment, the first and second coupling elements of first type are, in each case,—consequently also the oscillation exciter held thereby—arranged in the region of, for instance, half the free oscillatory length of the respective measuring tubes. By means of the two coupling elements $25_1$, $25_2$ of first type holding the at least one oscillation exciter, it can be assured in very effective, equally as well very simple, manner, that the exciter force generated by means of the oscillation exciter $5_1$ can effect equal frequency torsion—and bending oscillations of the measuring tubes, with the oscillations having a fixed phase relationship relative to one another.

Additionally, in a further embodiment of the invention, particularly also for the mentioned case, in which the first oscillation exciter 51 is of electrodynamic type, a permanent magnet serving as a component of the oscillation exciter is held to the first measuring tube by means of the coupling element of first type—here also serving as a lever arm effecting torsional moments acting on the first measuring tube—affixed to the first measuring tube, for instance, at a, distal first end of the first coupling element $25_1$ of first type removed from the first measuring tube. Furthermore, also a cylindrical coil permeated by the magnetic field of said permanent magnet and serving as another component of the oscillation exciter is held to the second measuring tube by means of the coupling element of first type—here also serving as a lever arm effecting torsional moments acting, respectively, on the second and fourth measuring tubes—affixed on the tube arrangement to the second and to the fourth measuring tubes, for instance, at a, distal first end of the second coupling element $25_2$ of first type removed from the second measuring tube.

According to an additional embodiment of the invention, the at least one driver signal $i_{exc1}$ is additionally so embodied, that it, at least at times, thus at least over a period of time sufficient for ascertaining at least one viscosity, measured value, is periodically variable and/or variable with at least one signal frequency corresponding to an eigenfrequency of a natural mode of oscillation of the tube arrangement, consequently the torsional oscillation, resonance frequency of the wanted mode selected for the measuring. Moreover, according to an additional embodiment of the invention, also the exciter forces produced by means of the second oscillation exciter (here, exciter forces periodic at least over a period of time sufficiently long for ascertaining a viscosity-measured value) are variable with signal frequency corresponding to at least eigenfrequency of a natural mode of oscillation of the tube arrangement.

The at least one driver signal and, insofar, the therewith produced, exciter forces $F_{exc1}$ can, in such case, in manner known, per se, to those skilled in the art, e.g. by means of an electrical current—and/or voltage control circuit provided in the already mentioned measuring—and operating electronics, be tuned as regards their amplitude and, e.g. by means of a phase control loop (PLL) likewise provided in the transmitter electronics, as regards their frequency (compare, for this, for example, also U.S. Pat. No. 4,801,897 or U.S. Pat. No. 6,311,136), so that thus the driver signal has a variable maximum voltage level and/or a variable maximum electrical current level, particularly such also correspondingly matched to the actually required excitation power. In such case, the first driver signal $i_{exc1}$ can also be so embodied, that it has a plurality of signal components of mutually differing signal frequencies, and that at least one of the signal components, for instance, a signal component dominating as regards signal power. The first driver signal $i_{exc1}$ has a signal frequency corresponding to an eigenfrequency of a natural mode of oscillation of the tube arrangement, for example, thus that eigenfrequency of the selected wanted mode, consequently that of the natural torsional oscillation mode of the tube arrangement, in which all four measuring tubes execute opposite-equal torsional oscillations.

According to a further development of the invention, the transmitter electronics is additionally designed to supply the exciter mechanism electrical excitation power also by means of a variable and/or, at least at times, periodic, second electrical driver signal $i_{exc2}$, for example, having at least one signal frequency corresponding to an eigenfrequency of a natural mode of oscillation of the tube arrangement, so that the exciter mechanism, as a result of this, also converts electrical excitation power, then also dependent on a voltage level and an electrical current level also of the second driver signal, as fed by means of the second driver signal, at least at times, into the mentioned torsional oscillations of the first measuring tube and the thereto opposite-equal torsional oscillations of the second measuring tube, as well as the torsional oscillations of the third measuring tube and the thereto opposite-equal torsional oscillations of the fourth measuring tube. The second driver signal can, in such case, likewise have a plurality of signal components of mutually differing signal frequencies, of which at least one signal component—, for instance, a signal component dominating as regards signal power—has a signal frequency corresponding to an eigenfrequency of a natural mode of oscillation of the tube arrangement, especially an eigenfrequency of a natural torsional oscillation mode of the tube arrangement, in which the measuring tubes, in each case, execute torsional oscillations with a single oscillation antinode. According to an additional embodiment of the invention, the second electrical driver signal $i_{exc2}$ (especially one produced simultaneously to the first driver signal) is, as regards at least one signal frequency, equal to the first driver signal, especially in such a manner, that a signal component of the first driver signal dominating as regards electrical current level has the same frequency as a signal component of the second driver signal dominating as regards electrical current level. In supplementation thereto, it is additionally provided, that the second electrical driver signal is fed into the exciter mechanism, at least at times, phase-shifted relative to the first driver signal, for example, by a phase angle lying in the range of 90° to 180° or by a phase angle of exactly 180 deg, or at least the two driver signals are so arranged, at least at times, as regards their phase relationship relative to one another, that the electrical current level dominating signal component of the first driver signal has, for example, a phase angle lying in a range of 90° to 180° lies or exactly 180° relative to the maximum electrical current level dominating signal component of the second driver signal, or, that is to say, phase-shifted as regards the signal power dominating signal components. Moreover, it can be quite advantageous to make the second electrical driver signal variable, in given cases, also adjustable during operation, as regards its maximum voltage level and/or its maximum electrical current level. Alternatively, or in supplementation, to the application of driver signals phase shifted relative to one another, according to an additional embodiment of the invention, it is provided that the second electrical driver signal is supplied into the exciter mechanism, at least at times, with a smaller maximum electrical current level in comparison to the first driver signal, at least, however, the two driver signals are so matched relative to one another, that the signal component of the first driver signal dominating as regards the electrical current level has, at least at times, a signal power, which is, for example, larger by more than 30%, than the signal power of the signal component of the second driver signal dominating as regards the electrical current level, so that, as a result, the exciter force $F_{exc1}$ produced by means of the first oscillation exciter, at least at times, has a size, which is different from a size of the exciter force $F_{exc2}$ produced by means of the second oscillation exciter, and/or that the torsional moment produced by means of the first oscillation exciter lastly likewise in the first and second measuring tubes, in each case, has, in each case, at least at times, a magnitude, which is different from a magnitude of a torsional moment produced by means of the second oscillation exciter simultaneously in, respectively, the third and fourth measuring tubes.

According to an additional embodiment of the invention, tube and the thereon acting exciter mechanism are so embodied and the at least one fed driver signal $i_{exc1}$, at least at times, so matched to tube and exciter mechanism, that each of the measuring tubes, excited by the exciter mechanism, during operation, at least at times, executes bending oscillations, for example, bending oscillations in a bending oscillation, fundamental mode having a single oscillatory antinode, in given cases, also simultaneously with the actively excited torsional oscillations. The bending oscillations can, in such case, be coupled, for example, in each case, with torsional oscillations of equal frequency thereto, for instance, opposite-equal torsional oscillations in a torsional oscillation, fundamental mode having a single oscillatory antinode. According to a further embodiment of the invention, the measuring tubes are excited by means of the exciter mechanism 5 during operation at least partially to bending oscillations, which have a bending oscillation frequency, which is approximately equal to an instantaneous mechanical resonance frequency of the measuring tubes, or the therewith formed, tube arrangement, or which lies at least in the vicinity of such an eigen- or resonance frequency. The instantaneous, mechanical bending oscillation, resonance frequencies are, as is known, in special measure, dependent on size, shape and material of the measuring tubes $18_1$, $18_2$, particularly, however, also on an instantaneous density of the medium flowing through the measuring tubes and can, insofar, be variable during operation of the measuring transducer within a wanted-frequency band of quite a few hertz. In the case of exciting the measuring tubes to bending oscillation resonance frequency, on the one hand, on the basis of the instantaneously excited oscillation frequency, supplementally also an average density of the medium flowing instantaneously through the measuring tubes can be easily ascertained. On the other hand, in this way, also the electrical power instantaneously required for maintaining the excited oscillations can be minimized.

Especially, the measuring tubes $18_1$, $18_2$, $18_3$, $18_4$, driven by the exciter mechanism 5, additionally, are caused to oscillate, at least at times, with essentially equal oscillation frequency, especially at a shared natural mechanical eigenfrequency of the tube arrangement. Especially suited here is a bending oscillation, fundamental mode naturally inherent to each of the measuring tubes, and having at minimum bending oscillation, resonance frequency, exactly one bending-oscillation antinode. For example, the measuring tubes, can be excited during operation by the thereto held, electromechanical exciter mechanism 5 to bending oscillations, especially at an instantaneous mechanical eigenfrequency of the tube arrangement formed by means of the measuring tubes, in the case of which they—at least predominantly—are caused to oscillate laterally deflected in a respective plane of oscillation and, as directly evident from the combination of FIGS. 1, 3, 4 and 5, with essentially opposite phase to one another. This especially in such a manner, that each of the measuring tubes, executes during operation, at the same time, vibrations embodied, at least at times, and/or at least partially, in each case, as bending oscillations about a measuring tube, longitudinal axis imaginarily connecting the first and the, in each case, associated second measuring tube end of the respective measuring tube, wherein the measuring tube, longitudinal axes in the measuring system of the invention with mutually parallel measuring tubes, extend equally parallel to one another, as the measuring tubes, and, moreover, also essentially parallel to an imaginary longitudinal axis of the total measuring transducer imaginarily connecting the two flow dividers and extending through a center of mass of the tube arrangement. In other words, the measuring tubes can, as quite usual in the case of measuring transducers of vibration-type, be caused to oscillate, in each case, at least sectionally in a bending oscillation mode in the manner of a string clamped at both sides. As a result of medium flowing through the measuring tubes excited to bending oscillations, there are induced therein additionally also Coriolis forces dependent on the mass flow, which effect, in turn, additional deformations of the measuring tubes, which correspond to higher oscillation modes of the measuring tubes—the so-called Coriolis mode—, and which are registerable by sensor. In advantageous manner, the oscillatory behavior of the tube arrangement formed by means of the four measuring tubes $18_1$, $18_2$, $18_3$, $18_4$,—together with the exciter mechanism and the sensor arrangement—, as well as also the driver signals controlling the exciter mechanism can, in such case, additionally be so matched to one another, that, as already indicated, at least the actively excited oscillations of the measuring tubes $18_1$, $18_2$, $18_3$, $18_4$, are so embodied, that the first and the second measuring tubes $18_1$, $18_2$ execute both torsional oscillations of essentially opposite phase to one another, thus opposite-equal torsional oscillations with an opposing phase shift of, for instance, 180°, as well as also bending oscillations of essentially opposite phase to one another and that the third and the fourth measuring tubes $18_3$, $18_4$ execute both torsional oscillations of essentially opposite phase to one another, thus opposite-equal torsional oscillations with an opposing phase shift of, for instance, 180°, as well as also bending oscillations of essentially opposite phase to one another.

For the mentioned case, in which the measuring transducer has coupling elements $25_1$, $25_2$ of first type, besides the first oscillation exciter $5_1$ also the second oscillation exciter $5_2$ can be correspondingly held thereto, for example, also in such a manner, that, as directly evident from FIG. 1a, 1b, 1c, or 4, a minimum distance between the first and second oscillation exciters $5_1$, $5_2$, in total, more than 2.5-times, as much as possible, however, at most 4-times as large as a pipe outer diameter of the measuring tubes $18_1$, $18_2$, $18_3$, $18_4$, at least, however, of the first measuring tube $18_1$. In this way, as a whole, an optimal exploitation of the space available in the interior of the transducer housing $7_1$, as well as also a high effectiveness of the oscillation exciter $5_1$, $5_2$, are attainable. Particularly also for the mentioned case, in which both the first as well as also the second oscillation exciters are of electrodynamic type, in an additional embodiment of the invention, a permanent magnet serving as a component of the second oscillation exciter is held affixed to the first and third measuring tubes by means of the first coupling element of first type, and a cylindrical coil serving as another component of the oscillation exciter and permeated by the magnetic field of said permanent magnet is held affixed to the second and fourth measuring tubes by means of the second coupling element of first type. In advantageous manner, the first and second coupling elements $25_1$, $25_2$ of first type, in such case, are additionally so placed in the measuring transducer, that both a center of mass of the first coupling element $25_1$ of first type as well as also a center of mass of the second coupling element $25_2$ of first type lie within an imaginary cross sectional plane of the tube arrangement, in which extend both the line of action of the exciter forces produced by the first oscillation exciter, as well as also the line of action of the exciter forces produced by the second oscillation exciter. As a result, thus, in such case, each of the, especially equally constructed, oscillation exciters $5_1$; $5_2$, is, in each case, equally held on the two coupling elements $25_1$, $25_2$ of first type lying opposite one another, so that thus the measuring transducer quite resembles that illustrated in the initially mentioned WO-A 96/08697 or US-A 2010/0050783, however, among other things, with the major difference, that, in the case of the measuring transducer of the measuring system of the invention, among other things, the exciter forces $F_{exc1}$ produced by means of the first oscillation exciter act relative to the exciter forces $F_{exc2}$ produced by means of the second oscillation exciter at least partially and/or, at least at times, oppositely and/or with different intensity on the tube arrangement and, as a result of this, torsional oscillations of the measuring tubes are actively excited. Additionally, in the case of application of the second oscillation exciter according to an additional embodiment of the invention, it is provided that the second driver signal $i_{exc2}$ is fed to the second oscillation exciter, or electrical excitation power correspondingly to be converted therein is fed in, by the fact that a second exciter current flows through the cylindrical coil of the second oscillation exciter driven by a variable second exciter voltage provided by means of the second driver signal.

As evident from FIGS. 1a, 1b, 1c, 2, 3 and 5 and usual in the case of measuring transducers of the type being discussed, there is provided in the measuring transducer 11 additionally a sensor arrangement 19 formed by means of at least a first oscillation sensor, for example, an electrodynamic, first oscillation sensor, reacting to, for example, inlet- or outlet-side, vibrations, particularly also to the opposite-equal torsion oscillations or torsion/bending oscillations, at least of the measuring tubes $18_1$, $18_2$ excited by means of the exciter mechanism 5. The, for example, electrodynamic, sensor arrangement 19 formed of the first oscillation sensor 191, registers, for example, differentially, mechanical oscillations, particularly also torsional oscillations or torsion/bending oscillations, of the measuring tubes, and produces, for representing mechanical oscillations, particularly torsional oscillations, in given cases, also bending oscillations, of the measuring tubes, at least one oscillation measurement signal $u_{sens1}$, which represents at least partially torsional oscillations of the first measuring tube $18_1$, particularly also the excited torsional oscillations of the same relative to opposite-equal torsional oscillations of the second measuring tube $18_2$, and which as regards at least one signal parameter, for example, a frequency, a signal amplitude, consequently a signal voltage, and/or a phase relationship relative to the at least one driver signal $i_{exc1}$, is influenced by the measured variable to be registered, such as, for instance, the viscosity of the medium, the density and the mass flow rate.

In an additional embodiment of the invention, the sensor arrangement is formed by means of a first oscillation sensor $19_1$, for example, an electrodynamic, first oscillation sensor, differentially registering torsional oscillations or torsion/bending oscillations of the first measuring tube $18_1$ relative to the second measuring tube $18_2$ as well as by a second oscillation sensor $19_2$, for example, an electrodynamic, second oscillation sensor, differentially registering torsional oscillations or torsion/bending oscillations of the first measuring tube $18_1$ relative to the second measuring tube $18_2$, which two oscillation sensors, reacting, in each case, to movements of the measuring tubes $18_1$, $18_2$, especially their torsional oscillation related twisting, or deformations, in given cases, however, also to lateral deflections of the measuring tubes, deliver the first oscillation measurement signal $U_{sens1}$, or a second oscillation measurement signal $U_{sens2}$. This, for example, also in such a manner, that the at least two oscillation measurement signals $U_{sens1}$, $U_{sens2}$ delivered by the sensor arrangement 19 have a phase shift relative to one another, which corresponds to, or is dependent thereon, the instantaneous mass flow rate of the medium flowing through the measuring tubes, as well as, in each case, have a signal frequency, which depends on an instantaneous density of the medium flowing in the measuring tubes. The first oscillation sensor $19_1$ can be placed, for example, on the inlet side of the of the tube arrangement and the second oscillation sensor on the outlet side of the tube arrangement, for instance, in such a manner, that the two, for example, one another equally constructed, oscillation sensors $19_1$, $19_2$—as in the case of measuring transducers of the type being discussed quite usual—are essentially equidistant in the measuring transducer 11 from the at least one oscillation exciter $5_1$, thus, in each case, equally as far removed from said oscillation exciter $5_1$. For assuring an as high as possible sensitivity of the measuring transducer, particularly also to the mass flow registered, in given cases, by means of bending oscillations of the measuring tubes, according to an additional embodiment of the invention, the measuring tubes the oscillation sensors are, in such case, so arranged in the measuring transducer, that a measuring length, $L_{19}$, of the measuring transducer corresponding to a minimum distance between the first oscillation sensor $19_1$ and the second oscillation sensor $19_2$ amounts to more than 500 mm, especially more than 600 mm.

Moreover, the oscillation sensors of the sensor arrangement 19 can be of equal construction to the at least one oscillation exciter of the exciter mechanism 5, at least to the extent that they work analogously to its principle of action, for example, thus likewise are of electrodynamic type and/or are held on the measuring tubes, removed, respectively, from the imaginary first and second longitudinal section planes of the tube arrangement, by means of coupling elements of first type serving as lever arms. Accordingly, the measuring transducer, especially for the mentioned case, in which the at least one oscillation exciter is held by means of two coupling elements $25_1$, $25_2$ of first type on the at least two measuring tubes, additionally includes a third coupling element $25_3$ of first type, for example, a plate shaped, third coupling element, affixed to the first measuring tube, especially only to the first measuring tube and/or otherwise to no other measuring tube, for holding components of the first oscillation sensor, for instance, a cylindrical coil for producing an electrical voltage serving for forming the first oscillation signal, or a permanent magnet, and for transmitting to the oscillation sensor an oscillatory movement executed by the first measuring tube, particularly also for converting a torsional oscillation movement executed by the first measuring tube into a translational movement dependent thereon, a fourth coupling element $25_4$ of first type, for example, a plate shaped, fourth coupling element or a fourth coupling element of equal construction to the third coupling element $25_3$ of first type, affixed to the second measuring tube, and/or otherwise to no other measuring tube, for holding components of the first oscillation sensor, for instance, a cylindrical coil or a permanent magnet, and for transmitting to the oscillation sensor an oscillatory movement executed by the second measuring tube, or for converting a torsional oscillation movement executed by the first measuring tube into a translational movement dependent thereon, a fifth coupling element $25_5$ of first type, for example, a plate shaped, fifth coupling element, affixed to the first measuring tube, and/or otherwise to no other measuring tube, for holding components of the second oscillation sensor, for instance, a cylindrical coil for producing an electrical voltage serving for forming the second oscillation signal, or a permanent magnet, and for transmitting to the oscillation sensor an oscillatory movement executed by the first measuring tube, or for converting a torsional oscillation movement executed by the first measuring tube into a translational movement dependent thereon, as well as a sixth coupling element $25_6$ of first type, for example, a plate shaped, sixth coupling element or a sixth coupling element of equal construction to the fifth coupling element $25_5$ of first type, affixed to the second measuring tube, and otherwise to no other measuring tube, for holding components of the second oscillation sensor, for instance, a cylindrical coil or a permanent magnet, and for transmitting to the oscillation sensor an oscillatory movement executed by the second measuring tube, or for converting a torsional oscillation movement executed by the first measuring tube into a translational movement dependent thereon.

In a further development of the invention, the sensor arrangement 19 is additionally formed by means of an inlet-side third oscillation sensor $19_3$, especially an electrodynamic, third oscillation sensor and/or a third oscillation sensor differential registering oscillations of the first measuring tube $18_3$ relative to the second measuring tube $18_4$, as well as an outlet-side fourth oscillation sensor $19_4$, especially an electrodynamic, fourth oscillation sensor and/or a fourth oscillation sensor differential registering oscillations of the first measuring tube $18_3$ relative to the second measuring tube $18_4$. For further improving signal quality, as well as also for simplifying the transmitter electronics 12 receiving the measurement signals, furthermore, the first and third oscillation sensors $19_1$, $19_3$, in the case of electrodynamic oscillation sensors can have their respective cylindrical coils electrically serially interconnected, for example, in such a manner, that a common oscillation measurement signal represents inlet-side oscillations of the first measuring tube $18_1$ relative to the second measuring tube $18_2$. Alternatively, or in supplementation, also the second and fourth oscillation sensors $19_2$, $19_4$, in the case of electrodynamic oscillation sensors, can have their respective cylindrical coils electrically serially interconnected in such a manner, that a common oscillation measurement signal of both oscillation sensors $19_2$, $19_4$ represents outlet-side oscillations of the first measuring tube $18_1$ relative to the second measuring tube $18_2$. Additionally, the sensor arrangement is, in such case, so embodied, that each of the $19_1$; $19_2$; $19_3$; $19_4$, for example, also oscillation sensors equally constructed to one another, is, in each case, held on two coupling elements $25_3$, $25_4$; $25_5$, $25_6$ of first type lying opposite one another.

For the aforementioned case, in which the, in given cases, equally constructed, oscillation sensors of the sensor arrangement 19 are to register oscillations of the measuring tubes differential and electrodynamically, additionally each of the oscillation sensors is, in each case, formed by means of a permanent magnet held—, for instance, by means of one of the mentioned coupling elements of first type—on one of the measuring tubes and a cylindrical coil permeated by the magnetic field of the permanent magnet, and held on the, in each case, other measuring tube—, for instance, by means of one of the mentioned coupling elements of first type—. In the case of four oscillation sensors $19_1$; $19_2$; $19_3$; $19_4$, these can e.g. be arranged in advantageous manner in the measuring transducer, such that, as directly evident from the combination of FIGS. 1a, 1b, 1c, 4, and 6, a minimum distance between the first and third oscillation sensors $19_1$, $19_3$, or the second and fourth oscillation sensors $19_2$, $19_4$ is, in each case, larger than twice the pipe outer diameter of the first measuring tube.

It is to be noted here additionally, that although the oscillation sensors of the sensor arrangement 19 illustrated in the example of an embodiment are, in each case, of electrodynamic type, thus, in each case, formed by means of a cylindrical magnet coil affixed on one of the measuring tubes and a therein plunging, permanent magnet affixed on an oppositely lying measuring tube—alternatively or in supplementation—also other oscillation sensors known to those skilled in the art, such as e.g. optoelectronic oscillation sensors, can be used for forming the sensor arrangement. Furthermore, as quite usual in the case of measuring transducers of the type being discussed, supplementally to the oscillation sensors, other, especially auxiliary—, or disturbance variables registering, sensors can be provided in the measuring transducer, such as e.g. acceleration sensors, pressure sensors and/or temperature sensors, by means of which, for example, the ability of the measuring transducer to function and/or changes of the sensitivity of the measuring transducer to the primary measured variable to be registered, especially the viscosity, the density and, in given cases, also the mass flow rate, as a result of cross sensitivities, or external disturbances, can be monitored and, in given cases, correspondingly compensated.

The exciter mechanism 5 and the sensor arrangement 19 are additionally, as usual in the case of such measuring transducers, particularly also for the purpose of transmission the at least one driver signal $i_{exc1}$, or the at least one oscillation measurement signal $u_{sens1}$, coupled in suitable manner, for example, by means of corresponding cable connections, with the driver circuit Exc and, respectively, the measuring- and evaluating circuit μC, both of which are correspondingly provided in the transmitter electronics, and these are also connected with one another during operation for data communication. The driver circuit Exc serves, as already mentioned, especially, on the one hand, for producing the driver signal $i_{exc1}$, for example, controlled as regards exciter current and/or exciter voltage, and ultimately driving the exciter mechanism 5. On the other hand, the measuring- and evaluating circuit μC receives the at least one oscillation measurement signal $U_{sens1}$ of the sensor arrangement 19 and generates therefrom, desired, measured values, thus those representing the viscosity η to be measured and/or the Reynolds number Re of the flowing medium ($X_\eta$; $X_{Re}$), or also such measured values, as a mass flow rate, a totaled mass flow and/or a density rho of the medium to be measured. The so produced, measured values can, in given cases, be visualized onsite, for example, by means of the mentioned display, and operating, element HMI, and/or also sent to a measuring system superordinated, data processing system, in the form of digital measured data—, in given cases, suitably encapsulated in corresponding telegrams—and there correspondingly further processed. In an additional embodiment of the measuring system of the invention, the transmitter electronics is, especially, designed to generate, on the basis of electrical excitation power converted in the exciter mechanism, especially power dependent on a voltage level and an electrical current level of the first driver signal $i_{exc1}$—, insofar, of course, also "known" to the transmitter electronics—, thus, that part of said excitation power, which at least partially is converted into torsional oscillations of the at least two measuring tubes or at least partially into torsion/bending oscillations of the at least two measuring tubes, a measured value representing the viscosity of the flowing medium and/or a measured value representing the Reynolds number of the flowing medium. For additionally improving the accuracy with which the viscosity, or the Reynolds number is measured by means of the measuring system, it is, in supplementation thereto, additionally provided, that the transmitter electronics generates the measured value representing the viscosity of the flowing medium and/or a measured value representing the Reynolds number of the flowing medium by means of the first oscillation signal, especially on the basis of a signal voltage and/or a signal frequency of the first oscillation signal. For the case, in which the exciter mechanism, as mentioned, is operated by means of two driver signals $i_{exc1}$, $i_{exc2}$, in given cases, also different from one another as regards signal amplitude and/or phase relationship, fed in at the same time, or the sensor arrangement delivers two or more oscillatory signals $u_{sens1}$, $u_{sens2}$, representing oscillations of the measuring tubes, of course, the, insofar, supplementally obtainable information concerning the current oscillatory behavior of the tube arrangement, consequently the medium decisively influencing said oscillatory behavior, correspondingly can be caused to enter into the ascertaining of the viscosity, or the Reynolds number, or the additional measured variables to be ascertained.

For the mentioned case, in which the sensor arrangement 19 has four oscillation sensors, it can be sufficient for the desired accuracy of measurement, to connect together individual oscillation sensors, e.g. pairwise, in order, so, correspondingly to reduce the number of the oscillation measurement signals supplied to the transmitter electronics and, associated therewith, the extent of circuitry needed for their processing. Equally, also the, in given cases, present, two oscillation exciter can be correspondingly brought together, for example, by a series connection of the two cylindrical coils, and be correspondingly operated by means of a single oscillatory signal. Thus, driver circuits directly known to those skilled in the art, especially driver circuits utilizing one channel, thus those delivering exactly one driver signal for the exciter mechanism, can also be used for the operating circuit driving the exciter mechanism. In case required, however, the oscillation measurement signals delivered by the two or more oscillation sensors can each be preprocessed and correspondingly digitized individually in separate measuring channels; equally, in case required, also the, in given cases, present, two or more oscillation exciters can be operated separately by means of separately produced, or output, driver signals.

The electrical connecting of the measuring transducer to the transmitter electronics can occur by means of corresponding connecting lines, which can be led out of the electronics housing $7_2$, for example, via cable feedthrough and directed, at least sectionally, within the transducer housing. The connecting lines can, in such case, be embodied, at least partially, as electrical line wires encased, at least sectionally in electrical insulation, e.g. in the form of "twisted pair"-lines, flat ribbon cables and/or coaxial cables. Alternatively thereto or in supplementation thereof, the connecting lines can, at least sectionally also be formed by means of conductive traces of a circuit board, especially a flexible circuit board, in given cases, a lacquered circuit board; compare, for this, also the initially mentioned U.S. Pat. Nos. 6,711,958 or 5,349,872. The, for example, also modularly embodied, transmitter electronics 12 can, as already mentioned, be accommodated, for example, in a—one part, or, for example, also multipart—separate electronics housing $7_2$, which is arranged removed from the measuring transducer or, as shown in, respectively FIGS. 1a, 1b, and 1c, affixed, for forming a single compact device, directly on the measuring transducer 1, for example, externally on the transducer housing $7_1$. In the case of the here illustrated example of an embodiment, consequently, there is placed on the transducer housing $7_1$ additionally a neck-like transition piece $7_3$ serving for holding the electronics housing $7_2$. Within the transition piece, there can be arranged additionally a feedthrough, for example, one manufactured by means of glass- and/or plastic potting compound, hermetically sealed and/or pressure resistant, for the electrical connecting lines between measuring transducer 11, thus, the therein placed oscillation exciters and—sensors, and the mentioned transmitter electronics 12.

As has already been multiply mentioned, the measuring transducer 11 and, insofar, also the measuring system of the invention are provided particularly also for measurements at high mass flows of more than 1200 t/h in a pipeline of large caliber of 100 mm or more. Taking this into consideration, according to an additional embodiment of the invention, the nominal diameter of the measuring transducer 11, which, as already mentioned, corresponds to a caliber of the pipeline, in whose course the measuring transducer 11 to be is used, is so selected, that it amounts to at least 100 mm, especially, however, is greater than 120 mm. Additionally, according to an additional embodiment of the measuring transducer, it is provided, that each of the measuring tubes $18_1$, $18_2$, in each case, has a caliber $D_{18}$, i.e. a tube inner diameter, amounting to more than 60 mm. Especially, the measuring tubes $18_1$, $18_2$ are additionally so embodied, that each has a caliber $D_{18}$ of more than 50 mm, especially more than 80 mm. Alternatively thereto or in supplementation thereof, the measuring tubes $18_1$, $18_2$, according to another embodiment of the invention, are additionally so dimensioned, that they have, in each case, a measuring tube length $L_{18}$ of at least 800 mm. The measuring tube length $L_{18}$ corresponds, in the here illustrated example of an embodiment with equal length measuring tubes $18_1$, $18_2$, in each case, to a minimum distance between the first flow opening $20_{1A}$ of the first flow divider $20_1$ and the first flow opening $20_{2A}$ of the second flow divider $20_2$. Especially, the measuring tubes $18_1$, $18_2$ are, in such case, so designed, that their measuring tube length $L_{18}$ is, in each case, greater than 1000 mm. Accordingly, there results at least for the mentioned case, in which the measuring tubes $18_1$, $18_2$, are of steel, in the case of which usually used wall thicknesses of over 0.6 mm has a mass of, in each case, at least 10 kg, especially more than 20 kg. Additionally, it is, however, desirable to keep the empty mass of each of the measuring tubes $18_1$, $18_2$, less than 40 kg.

In consideration of the fact that, as already mentioned, each of the measuring tubes $18_1$, $18_2$, in the case of measuring transducer of the invention, weighs well over 10 kg, and, in such case, as directly evident from the above dimensional specifications, can have a capacity of easily 5 l or more, the tube arrangement including the measuring tubes $18_1$, $18_2$, at least in the case of medium of high density flowing through, can reach a total mass of far beyond 40 kg. Especially in the case of the application of measuring tubes with comparatively large caliber $D_{18}$, large wall thickness and large measuring tube length $L_{18}$, the mass of the tube arrangement formed of the measuring tubes $18_1$, $18_2$ can be, however, also greater than 50 kg or at least with medium flowing through, e.g. oil or water, more than 60 kg. As a result of this, an empty mass $M_{11}$ of the measuring transducer, as a whole, amounts also to far more than 80 kg, and, in the case of nominal diameters $D_{11}$ of essentially greater than 100 mm, even more than 100 kg. As a result, in the case of the measuring transducer of the invention, a mass ratio $M_{11}/M_{18}$ of an empty mass $M_{11}$ of the total measuring transducer to an empty mass $M_{18}$ of the first measuring tube can easily be greater than 5, especially greater than 10.

In order, in the case of the mentioned high empty masses $M_{11}$ of the measuring transducer, to use the material applied therefor, as a whole, as optimally as possible and, insofar, to utilize the—most often also very expensive—material, as a whole, as efficiently as possible, according to an additional embodiment, the nominal diameter $D_{11}$ of the measuring transducer, matched to its empty mass $M_{11}$, is so dimensioned, that a mass to nominal diameter ratio $M_{11}/D_{11}$ of the measuring transducer 11, defined by a ratio of the empty mass $M_{11}$ of the measuring transducer 11 to the nominal diameter $D_{11}$ of the measuring transducer 11 is less than 1 kg/mm, especially as much as possible, however, less than 0.8 kg/mm. In order to assure a sufficiently high stability of the measuring transducer 11, the mass to nominal diameter ratio $M_{11}/D_{11}$ of the measuring transducer 11, at least in the case of use of the above mentioned, conventional materials is, however, to choose as much as possible greater than 0.3 kg/mm. Additionally, according to an additional embodiment of the invention for additionally improving the efficiency of the installed material, it is provided, that the mentioned mass ratio $M_{11}/M_{18}$ is kept smaller than 20. For creation of a nevertheless as compact as possible measuring transducer of sufficiently high oscillation quality factor and as little as possible pressure drop, according to an additional embodiment of the invention, the measuring tubes, matched to the above mentioned installed length $L_{11}$ of the measuring transducer 11, are so dimensioned, that a caliber to installed length ratio $D_{18}/L_{11}$ of the measuring transducer, defined by a ratio of the caliber $D_{18}$ at least of the first measuring tube to the installed length $L_{11}$ of the measuring transducer 11, amounts to more than 0.02, especially more than 0.05 and/or less than 0.1. Alternatively, or in supplementation, the measuring tubes $18_1$, $18_2$, matched to the above mentioned, installed length $L_{11}$ of the measuring transducer, are so dimensioned, that a measuring tube length to installed length ratio $L_{18}/L_{11}$ of the measuring transducer, defined by a ratio of the measuring tube length $L_{18}$ at least of the first measuring tube to the installed length $L_{11}$ of the measuring transducer, amounts to more than 0.5, especially more than 0.6 and/or less than 0.95, and/or that an oscillation length to measuring tube length ratio, $L_{18x}/L_{18}$, of the measuring transducer, defined by a ratio of the free oscillatory length, $L_{18x}$, of the first measuring tube to the measuring tube length, $L_{18}$, of the first measuring tube, amounts to more than 0.55, especially more than 0.6, and/or less than 0.95, especially less than 0.9.

In case required, mechanical stresses and/or vibrations possibly or at least potentially caused by the vibrating measuring tubes, especially measuring tubes, which are, in the mentioned manner, relatively large dimensioned, at the inlet side or at the outlet side in the transducer housing, e.g. can be minimized by providing that the measuring tubes $18_1$, $18_2$ are connected mechanically with one another at the inlet and outlet sides, in each case, by means of coupling elements $24_1$, $24_2$ serving as so-called node plates—in the following referred to as coupling elements of second type—. Moreover, by means of such coupling elements of second type, be it through their dimensioning and/or their positioning on the measuring tubes, mechanical eigenfrequencies of the measuring tubes and, thus, also mechanical eigenfrequencies of the inner part formed by means of the tube arrangement as well as thereon placed, additional components of the measuring transducer, such as, for instance, the oscillation sensors and oscillation exciters, and, insofar, also its oscillatory behavior, as a whole, can, with targeting, be influenced. The coupling elements of second type serving as node plates can, for example, be thin plates or washers, especially plates or washers manufactured of the same material as the measuring tubes, which are provided with bores corresponding, in each case, with the number and the outer dimensions of the measuring tubes to be coupled with one another, in given cases, supplementally slitted to the edge, so that the washers are first placed tightly on the respective measuring tubes $18_1$, or $18_2$ and, in given cases, thereafter then bonded with the respective measuring tubes, for example, by hard solder or welding. It can additionally, in the sense of a still simpler and still more exact adjusting of the oscillatory behavior of the measuring transducer, be quite of advantage, when the measuring transducer, as, for example, provided in US-A 2006/0150750, moreover, has still other coupling elements the aforementioned type, for example, thus, as a whole, 4, 6 or 8 such coupling elements of second type, serving for forming of inlet-, or outlet-side oscillation nodes for vibrations, especially bending oscillations, of the first measuring tube and for thereto opposite phase vibrations, especially bending oscillations, of the second measuring tube.

For creation of an as compact as possible measuring transducer of sufficiently high oscillation quality factor and high sensitivity in the case of as little as possible pressure drop, according to an additional embodiment of the invention, the measuring tubes $18_1$, $18_2$, matched on the mentioned free oscillatory length, are so dimensioned, that a caliber to oscillatory length ratio $D_{18}/L_{18x}$ of the measuring transducer, defined by a ratio of the caliber $D_{18}$ of the first measuring tube to the free oscillatory length $L_{18x}$ of the first measuring tube, amounts to more than 0.07, especially more than 0.09 and/or less than 0.15. Alternatively, or in supplementation, for this, according to an additional embodiment of the invention, the measuring tubes $18_1$, $18_2$, matched to the above mentioned installed length $L_{11}$ of the measuring transducer, are so dimensioned, that an oscillation length to installed length ratio $L_{18x}/L_{11}$ of the measuring transducer, defined by a ratio of the free oscillatory length $L_{18x}$ of the first measuring tube to the installed length $L_{11}$ of the measuring transducer, amounts to more than 0.55, especially more than 0.6 and/or less than 0.9. According to an additional embodiment of the invention, the oscillation sensors, matched on the free oscillatory length, are so arranged in the measuring transducer, that a measuring length to oscillatory length ratio of the measuring transducer, defined by a ratio of the mentioned measuring length of the measuring transducer to the free oscillatory length of the first measuring tube, amounts to more than 0.6, especially more than 0.65 and/or less than 0.95. According to an additional embodiment of the invention, the oscillation sensors, matched to the installed length of the measuring transducer, are so arranged in the measuring transducer, that a measuring length to installed length ratio of the measuring transducer, defined by a ratio of the measuring length to the installed length of the measuring transducer, amounts to more than 0.3, especially more than 0.4 and/or less than 0.7. Alternatively, or in supplementation, the oscillation sensors, in an additional embodiment of the invention, matched to the measuring tubes, are so placed in the measuring transducer, that a caliber to measuring length ratio, $D_{18}/L_{19}$, of the measuring transducer, defined by a ratio of the caliber $D_{18}$ of the first measuring tube to the measuring length $L_{19}$ of the measuring transducer, amounts to more than 0.05, especially more than 0.09. In an additional embodiment of the invention, the above mentioned, measuring length $L_{19}$ is kept less than 1200 mm.

Through the application of two measuring tubes flowed through in parallel, instead of, as previously, a single straight measuring tube, for the registering of measured variables, or of operating parameters serving for diagnosis of the measuring device, such as, for instance, the viscosity, the Reynolds number or an oscillation damping, which depend significantly on—, especially, by torsional oscillations producible—inner friction forces in the medium, it is, thus, also possible to manufacture, cost effectively, measuring transducers of the described type also in the case of large mass flow rates, or with large nominal diameters of far over 100 mm, on the one hand, with a high accuracy of measurement coupled with an acceptable pressure drop, especially of, for instance, 1 bar or less, and, on the other hand, to keep the installed mass, as well as also the empty mass, of such measuring transducers sufficiently in limits, that, in spite of large nominal diameter, the manufacture, transport, installation, as well as also operation can always still occur economically sensibly. Especially also by implementing previously explained measures further developing the invention—individually or also in combination—measuring transducers of the type being discussed can also in the case of large nominal diameter be so embodied and so dimensioned, that a mass ratio of the measuring transducer defined by a ratio of the mentioned empty mass of the measuring transducer to a total mass of the tube arrangement (formed by means of the measuring tubes) as well as all thereto held, additional components of the measuring transducer influencing the oscillatory behavior of the tube arrangement can be kept less than 3, especially less than 2.5.

The invention claimed is:

1. A measuring system for a medium flowing in a pipeline, said measuring system comprising:
    a measuring transducer of the vibration-type, through which medium flows during operation and which serves for producing oscillatory signals dependent on a viscosity of the flowing medium and/or dependent on a Reynolds number of the flowing medium; and
    a transmitter electronics electrically coupled with said measuring transducer for driving said measuring transducer and for evaluating oscillatory signals delivered by said measuring transducer,
    said measuring transducer including a transducer-housing, of which an inlet-side, first housing end is formed by means of an inlet-side first flow divider having exactly four, mutually spaced flow openings, and an outlet-side, second housing end by means of an outlet-side second flow divider having exactly four, mutually spaced flow openings,
    for conveying flowing medium, said measuring transducer including exactly four, straight measuring tubes connected, for forming a tube arrangement with four flow paths with parallel flow, with said first and second flow dividers, of which measuring tubes
    a first measuring tube, opens with an inlet-side, first measuring tube end into a first flow opening of said first flow divider and with an outlet-side, second measuring tube end into a first flow opening of said second flow divider,
    a second measuring tube, opens with an inlet-side, first measuring tube end opening into a second flow opening of said first flow divider and with an outlet-side, second measuring tube end into a second flow opening of said second flow divider,
    a third measuring tube, opens with an inlet-side, first measuring tube end into a third flow opening of said first flow divider and with an outlet-side, second measuring tube end into a third flow opening of said second flow divider, and
    a fourth measuring tube opens with an inlet-side, first measuring tube end opening into a fourth flow opening of said first flow divider and with an outlet-side, second measuring tube end into a fourth flow opening of said second flow divider; and
    said measuring transducer including an electromechanical exciter mechanism for exciting and maintaining mechanical oscillations of the four measuring tubes;
    wherein:
    said transmitter electronics is adapted to feed electrical excitation power into the exciter mechanism by means of a variable and/or, at least at times, periodic, first electrical driver signal supplied to the exciter mechanism; and
    said exciter mechanism is adapted to convert the electrical excitation power at least partially, both into torsional oscillations of said first measuring tube and into torsional oscillations of said second measuring tube opposite-equal to the torsional oscillations of said first measuring tube, as well as into torsional oscillations of said third measuring tube and into torsional oscillations of said fourth measuring tube opposite-equal to the torsional oscillations of said third measuring tube.

2. The measuring system as claimed in claim 1, wherein: said exciter mechanism includes at least a first oscillation exciter acting on at least two of said measuring tubes for converting electrical excitation power fed into said exciter mechanism into variable and/or periodic, mechanical exciter forces effecting the torsional oscillations of said first measuring tube and the torsional oscillations of said second measuring tube opposite-equal to the torsional oscillations of said first measuring tube.

3. The measuring system as claimed in claim 2, wherein: said first oscillation exciter includes a permanent magnet held on said first measuring tube by means of a coupling element affixed at least to said first measuring tube and serving as a lever arm for effecting torsional moments acting on said first measuring tube, and the first oscillation exciter includes a cylindrical coil permeated by the magnetic field of the permanent magnet and held on said second measuring tube by means of a coupling element affixed at least to said second measuring tube and serving as a lever arm for effecting torsional moments acting on said second measuring tube.

4. The measuring system as claimed in claim 2, wherein: the first driver signal is fed to the first oscillation exciter, in such a manner, that a first exciter current flows through its cylindrical coil driven by a variable first exciter voltage provided by means of said first driver signal.

5. The measuring system as claimed in claim 2, wherein: the tube arrangement shows a first imaginary longitudinal section plane, in which extend both a measuring tube, longitudinal axis of said first measuring tube, which imaginarily connects its first and second measuring tube ends, as well as also a measuring tube, longitudinal axis of said second measuring tube, which imaginarily connects its first and second measuring tube ends and is parallel to the measuring tube, longitudinal axis of said first measuring tube; and
the tube arrangement shows, spaced from, and parallel to, the first imaginary longitudinal section plane, a second imaginary longitudinal section plane, in which extend both a measuring tube, longitudinal axis of said third measuring tube, which imaginarily connects its first and second measuring tube ends, as well as also a measuring tube, longitudinal axis of said fourth measuring tube, which imaginarily connects its first and second measuring tube ends and is parallel to the measuring tube, longitudinal axis of said first measuring tube.

6. The measuring system as claimed in claim 5, wherein:
the tube arrangement shows a third imaginary longitudinal section plane lying between the first longitudinal section plane and second longitudinal section plane, spaced, in each case, from the first imaginary longitudinal section plane and from the second imaginary longitudinal section plane and, in each case, parallel to the first and second longitudinal section plane; and
said first oscillation exciter is adapted to convert electrical excitation power into exciter forces serving for exciting oscillations of said measuring tubes and being introduced into the tube arrangement along a line of action spaced from the third imaginary longitudinal section plane.

7. The measuring system as claimed in claim 6, wherein:
said first measuring tube has a caliber, which equals a caliber of said second measuring tube, and
said first oscillation exciter is so embodied and arranged in the measuring transducer, that the line of action, with which the exciter forces produced by said first oscillation exciter are introduced into the tube arrangement, has a perpendicular distance to the third imaginary longitudinal section plane of the tube arrangement, which is greater than a fourth of the caliber of said first measuring tube.

8. The measuring system as claimed in claim 6, wherein:
said exciter mechanism effects oscillations of said measuring tubes by the feature that an exciter force generated by means of said first oscillation exciter and acting on said first measuring tube is opposite to an exciter force generated at the same time by means of said first oscillation exciter and acting on said second measuring tube.

9. The measuring system as claimed in claim 5, wherein:
said exciter mechanism includes further a second oscillation exciter acting on said third and fourth measuring tubes for converting electrical excitation power fed into said exciter mechanism into variable and/or periodic, mechanical exciter forces effecting the torsional oscillations of said third measuring tube and the torsional oscillations of said fourth measuring tube opposite-equal to the torsional oscillations of said third measuring tube.

10. The measuring system as claimed in claim 9, wherein:
the second oscillation exciter includes a permanent magnet held at least on said third measuring tube by means of a coupling element affixed to said third measuring tube and serving as a lever arm for effecting torsional moments acting on said third measuring tube, and the second oscillation exciter includes a cylindrical coil permeated by the magnetic field of the permanent magnet and held at least on said fourth measuring tube.

11. The measuring system as claimed in claim 9, wherein:
said second oscillation exciter is placed in said measuring transducer on a side of the third imaginary longitudinal section plane of the tube arrangement facing away from said first oscillation exciter.

12. The measuring system as claimed in claim 9, wherein:
the tube arrangement has a third imaginary longitudinal section plane lying between the first longitudinal section plane and the second longitudinal section plane, spaced, in each case, from the first imaginary longitudinal section plane and from the second imaginary longitudinal section plane and, in each case, parallel to the first and second longitudinal section plane;
said first oscillation exciter is adapted to convert electrical excitation power, fed by means of the first driver signal, into exciter forces serving for exciting oscillations of said measuring tubes and being introduced into the tube arrangement along a line of action spaced from the third imaginary longitudinal section plane; and
said second oscillation exciter is adapted to convert electrical excitation power, fed by means of the second driver signal, into exciter forces serving for exciting oscillations of said measuring tubes and being introduced into the tube arrangement along a line of action spaced from the third imaginary longitudinal section plane and extending at least approximately parallel thereto.

13. The measuring system as claimed in claim 12, wherein:
the tube arrangement has, perpendicular to the third imaginary longitudinal section plane, an imaginary cross sectional plane, in which extend both, the line of action of the exciter forces produced by said first oscillation exciter, as well as also the line of action of the exciter forces produced by said second oscillation exciter.

14. The measuring system as claimed in claim 12, wherein:
said exciter mechanism is adapted to effect oscillations of said measuring tubes by the feature, that an exciter force generated by means of said second oscillation exciter and acting on said third measuring tube is opposite to an exciter force generated at the same time by means of said second oscillation exciter and acting on said fourth measuring tube.

15. The measuring system as claimed in claim 14, wherein:
said exciter mechanism is adapted to effect opposite-equal torsional oscillations of said measuring tubes by the features, that the exciter force generated by means of said first oscillation exciter and acting on said first measuring tube is oppositely directed to the exciter force generated at the same time by means of said second oscillation exciter and acting on said third measuring tube, and that the exciter force generated by means of said first oscillation exciter and acting on said second measuring tube is oppositely directed to the exciter force generated at the same time by means of said second oscillation exciter and acting on said fourth measuring tube.

16. The measuring system as claimed in claim 5, wherein:
the tube arrangement has a third imaginary longitudinal section plane lying between the first longitudinal section plane and second longitudinal section plane, spaced, in each case, from the first imaginary longitudinal section plane and from the second imaginary longitudinal section plane and, in each case, parallel to the first and second longitudinal section plane, and
said first oscillation exciter is adapted to convert electrical excitation power into exciter forces serving for exciting oscillations of said measuring tubes and being introduced into the tube arrangement along a line of action, said line of action being spaced from the first and third imaginary longitudinal section planes and said line of action extending transversely to said measuring tube, longitudinal axis of the first measuring tube and to said measuring tube, longitudinal axis of the second measuring tube.

17. The measuring system as claimed in claim 2, further comprising:

a first coupling element of the first type affixed to said first measuring tube as well as also to said third measuring tube, but to no other measuring tube, for holding components of said first oscillation exciter and for introducing an exciter force generated by means of said first oscillation exciter into said first measuring tube and/or for converting a exciter force generated by means of said first oscillation exciter into a torsional moment acting on said first measuring tube and a torsional moment acting on said third measuring tube; as well as a second coupling element of the first type affixed to said second measuring tube as well as also to said fourth measuring tube, but to no other measuring tubes, for holding components of said first oscillation exciter and for introducing an exciter force generated by means of said first oscillation exciter into said second measuring tube and/or for converting a exciter force generated by means of said first oscillation exciter into a torsional moment acting on said second measuring tube and into a torsional moment acting on said fourth measuring tube.

18. The measuring system as claimed in claim 17, wherein: said electromechanical exciter mechanism further includes a second oscillation exciter for acting on at least two of said measuring tubes for converting electrical excitation power fed into said exciter mechanism into variable and/or periodic, mechanical exciter forces effecting the torsional oscillations of said third measuring tube and the torsional oscillations of said fourth measuring tube opposite-equal to the torsional oscillations of said third measuring tube, and each of said first and second oscillation exciters is, in each case, held on said first and said second coupling elements of the first type.

19. The measuring system as claimed in claim 17, wherein: said first oscillation exciter includes a permanent magnet and a cylindrical coil permeated by the magnetic field of said permanent magnet, said permanent magnet of the first oscillation exciter being affixed to said first coupling element of the first type, and said cylindrical coil of said first oscillation exciter being affixed to said second coupling element of the first type.

20. Th measuring system as claimed in claim 19, wherein: said permanent magnet of said first oscillation exciter is affixed to a distal first end of said first coupling element of the first type removed from said first measuring tube, and the cylindrical coil of said first oscillation exciter is affixed to a distal first end of said second coupling element of the first type removed from said second measuring tube.

21. The measuring system as claimed in claim 17, wherein: said first and said second coupling elements of the first type are so placed in said measuring transducer, that both a center of mass of said first coupling element of the first type as well as also a center of mass of said second coupling element of the first type lie within the cross sectional plane, in which extend both a line of action of the exciter forces being produced by said first oscillation exciter and serving for exciting oscillations of said measuring tubes, as well as also a line of action of the exciter forces being produced by said second oscillation exciter and serving for exciting oscillations of said measuring tubes.

22. The measuring system as claimed in claim 1, wherein: said exciter mechanism effects both, bending oscillations of said first measuring tube about its measuring tube, longitudinal axis and bending oscillations of said second measuring tube about its measuring tube, longitudinal axis, opposite-equal to the bending oscillations of said first measuring tube, as well as also bending oscillations of said third measuring tube about its measuring tube, longitudinal axis and bending oscillations of said fourth measuring tube about its measuring tube, longitudinal axis, opposite-equal to the bending oscillations of said third measuring tube.

23. The measuring system as claimed in claim 22, wherein: the tube arrangement is so embodied, that at least one eigenfrequency of natural bending oscillations of said first measuring tube equals an eigenfrequency of natural torsional oscillations of said first measuring tube, and that at least one eigenfrequency of natural bending oscillations of said second measuring tube equals an eigenfrequency of natural torsional oscillations of said second measuring tube.

24. The measuring system as claimed in claim 23, wherein: said exciter mechanism is adapted to excite each of said measuring tubes to execute opposite-equal bending oscillations coupled with thereto, in each case, equal frequency torsional oscillations.

25. The measuring system as claimed in claim 1, wherein: said first measuring tube has a caliber, which equals a caliber of said second measuring tube, a caliber of said third measuring tube as well as a caliber of said fourth measuring tube.

26. The measuring system as claimed in claim 1, wherein: the first driver signal includes a plurality of signal components of mutually differing signal frequencies, at least one of said signal components of the first driver signal showing a signal frequency corresponding to an eigenfrequency of a natural mode of oscillation of the tube arrangement, in which natural mode of oscillation each of said four measuring tubes executes torsional oscillations.

27. The measuring system as claimed in claims 1, wherein: said transmitter electronics is adapted to feed electrical excitation power into said exciter mechanism also by means of a variable and/or, at least at times, periodic, second electrical driver signal supplied to said exciter mechanism.

28. The measuring system as claimed in claim 27, wherein: said exciter mechanism is adapted to convert electrical excitation power fed by means of the second driver signal into torsional oscillations of said third measuring tube and into torsional oscillations of said fourth measuring tube opposite-equal to the torsional oscillations of said third measuring tube.

29. The measuring system as claimed in claim 27, wherein: the second driver signal includes a plurality of signal components of mutually differing signal frequencies, at least one of said signal components of the second driver signal showing a signal frequency corresponding to an eigenfrequency of a natural mode of oscillation of the tube arrangement, in which natural mode of oscillation the at least two measuring tubes execute opposite-equal torsional oscillations.

30. The measuring system as claimed in claim 27, wherein: the second driver signal is fed to said second oscillation exciter in such a manner, that a second exciter current flows through its cylindrical coil driven by a variable second exciter voltage provided by means of the second driver signal.

31. The measuring system as claimed in claim 1, wherein: said transmitter electronics is adapted to generate, on the basis of electrical excitation power transformed in said exciter mechanism, a measured value representing viscosity of the flowing medium and/or a measured value representing the Reynolds number of the flowing medium.

32. The measuring system as claimed in claim 31, wherein: said transmitter electronics is adapted to generate by means of the first oscillation signal the measured value representing the viscosity of the flowing medium and/or the measured value representing the Reynolds number of the flowing medium.

33. The measuring system as claimed in claim 1, wherein: said measuring transducer further includes a sensor arrangement for the registering of mechanical oscillations and for producing at least a first oscillation signal representing mechanical oscillations of said measuring tubes.

34. The measuring system as claimed in claim 33, wherein: the first oscillatory signal delivered by said sensor arrangement represents, at least partially, torsional oscillations of said first measuring tube.

35. The measuring system as claimed in claim 33, wherein: said sensor arrangement includes at least a first oscillation sensor for registering mechanical oscillations of said measuring tubes and for producing the first oscillation signal.

36. The measuring system as claimed in claim 35, wherein: said first oscillation sensor includes: a permanent magnet held on said first measuring tube and a cylindrical coil permeated by the magnetic field of the permanent magnet and held on said second measuring tube for producing an electrical voltage serving for forming the first oscillation signal.

37. The measuring system as claimed in claim 36, wherein: said sensor arrangement includes further: a second oscillation sensor for registering mechanical oscillations of said measuring tubes and for producing at least a second oscillation signal representing mechanical oscillations.

38. The measuring system as claimed in claim 37, wherein: said second oscillation sensor includes: a permanent magnet held on said first measuring tube and a cylindrical coil permeated by the magnetic field of said permanent magnet and held on said second measuring tube for producing an electrical voltage serving for forming the second oscillation signal.

39. The measuring system as claimed in claim 37, wherein: said sensor arrangement includes further: a third oscillation sensor for registering mechanical oscillations of said measuring tubes and a fourth oscillation sensor for registering of said measuring tubes.

40. The measuring system as claimed in claim 39, wherein: said third oscillation sensor includes a permanent magnet held on said first measuring tube and said third oscillation sensor includes a cylindrical coil permeated by the magnetic field of said permanent magnet and held on said second measuring tube; and
said fourth oscillation sensor includes a permanent magnet held on the first measuring tube and said fourth oscillation sensor includes a cylindrical coil permeated by the magnetic field of said permanent magnet and held on said second measuring tube.

41. The measuring system as claimed in claim 40, wherein: said first oscillation sensor includes a cylindrical coil and said second oscillation sensor includes a cylindrical coil, said cylindrical coil of said first oscillation sensor and said cylindrical coil of said third oscillation sensor being connected electrically in series, and said cylindrical coil of said second oscillation sensor and said cylindrical coil of said fourth oscillation sensor being connected electrically in series.

42. The measuring system as claimed in claim 39, wherein: said transmitter electronics is adapted to generate a measured value representing the viscosity of the flowing medium, and/or a measured value representing the Reynolds number of the flowing medium, by means of the third oscillation signal, as well as by means of the fourth oscillation signal.

43. The measuring system as claimed in claim 37, wherein: said transmitter electronics is adapted to generate a measured value representing the viscosity of the flowing medium, and/or a measured value representing the Reynolds number of the flowing medium, by means of the second oscillation signal.

44. The measuring system as claimed in claim 1, wherein: said measuring transducer further comprises a transducer-housing, of which an inlet-side, first housing end is formed by means of said first flow divider and an outlet-side second housing end is formed by means of said second flow divider.

45. The measuring system as claimed in claim 1, wherein: said measuring transducer, except for said four measuring tubes, has no further measuring tubes serving for conveying flowing medium and allowed to vibrate during operation.

46. The use of a measuring system as claimed in claim 1, for measuring a mass flow and/or a density and/or a viscosity and/or a Reynolds number of a medium flowing in a process line.

47. The measuring system as claimed in claim 1, wherein: said exciter mechanism is adapted to convert the electrical excitation power at least partially, both into torsional oscillations of said first measuring tube and into torsional oscillations of said second measuring tube opposite-equal to the torsional oscillations of said first measuring tube, as well as into torsional oscillations of said third measuring tube and into torsional oscillations of said fourth measuring tube opposite-equal to the torsional oscillations of said third measuring tube in such a manner, that a middle tube segment of said first measuring tube executes rotary oscillations about an imaginary torsional oscillation axis perpendicular to a cross section of said tube segment, a middle tube segment of said second measuring tube executes rotary oscillations about an imaginary torsional oscillation axis perpendicular to a cross section of said tube segment, a middle tube segment of said third measuring tube executes rotary oscillations about an imaginary torsional oscillation axis perpendicular to a cross section of said tube segment and a middle tube segment of said fourth measuring tube executes rotary oscillations about an imaginary torsional oscillation axis perpendicular to a cross section of said tube segment.

48. The measuring system as claimed in claim 1, wherein: said exciter mechanism is adapted to convert the electrical excitation power at least partially, both into torsional oscillations of said first measuring tube and into torsional oscillations of said second measuring tube opposite-equal to the torsional oscillations of said first measuring tube, as well as into torsional oscillations of said third measuring tube and into torsional oscillations of said fourth measuring tube opposite-equal to the torsional oscillations of said third measuring tube in such a manner, that simultaneously each of said measuring tubes executes torsional oscillations in a torsional oscillation, fundamental mode having a single oscillatory antinode.

\* \* \* \* \*